(12) United States Patent
Melnyk et al.

(10) Patent No.: US 10,844,008 B2
(45) Date of Patent: Nov. 24, 2020

(54) COMPOUNDS, PHARMACEUTICAL COMPOSITION AND THEIR USE IN TREATING NEURODEGENERATIVE DISEASES

(71) Applicants: UNIVERSITE DE LILLE 2 DROIT ET SANTE, Lille (FR); CENTRE HOSPITALIER REGIONAL ET UNIVERSITAIRE DE LILLE (CHRU), Lille (FR)

(72) Inventors: Patricia Melnyk, Annoellin (FR); Patrick Vermersch, Marcq en Baroeul (FR); Pascal Carato, Ronchin (FR); Bénédicte Oxombre-Vanteghem, Arneke (FR); Héléne Zephir, Lille (FR); Marion Donnier-Marechal, St Jean de Moirans (FR)

(73) Assignees: UNIVERSITE DE LILLE 2 DROIT ET SANTE, Lille (FR); CENTRE HOSPITALIER REGIONAL ET UNIVERSITAIRE DE LILLE (CHRU), Lille (FR)

( * ) Notice: Subject to any disclaimer, the term of this patent is extended or adjusted under 35 U.S.C. 154(b) by 0 days.

(21) Appl. No.: 16/205,637

(22) Filed: Nov. 30, 2018

(65) Prior Publication Data
US 2019/0092721 A1    Mar. 28, 2019

Related U.S. Application Data

(62) Division of application No. 15/317,742, filed as application No. PCT/EP2015/063370 on Jun. 15, 2015, now Pat. No. 10,179,761.

(30) Foreign Application Priority Data

Jun. 16, 2014    (EP) .................................... 14305919

(51) Int. Cl.

| | | |
|---|---|---|
| C07C 233/78 | (2006.01) | |
| C07C 255/57 | (2006.01) | |
| C07C 311/37 | (2006.01) | |
| C07C 211/27 | (2006.01) | |
| C07C 211/29 | (2006.01) | |
| C07C 235/50 | (2006.01) | |
| C07C 237/20 | (2006.01) | |
| C07C 237/34 | (2006.01) | |
| C07D 209/08 | (2006.01) | |
| A61K 49/00 | (2006.01) | |
| C07C 237/10 | (2006.01) | |
| C07C 255/60 | (2006.01) | |
| C07D 209/44 | (2006.01) | |

(52) U.S. Cl.
CPC ............ *C07C 233/78* (2013.01); *A61K 49/00* (2013.01); *C07C 211/27* (2013.01); *C07C 211/29* (2013.01); *C07C 235/50* (2013.01); *C07C 237/10* (2013.01); *C07C 237/20* (2013.01); *C07C 237/34* (2013.01); *C07C 255/57* (2013.01); *C07C 255/60* (2013.01); *C07C 311/37* (2013.01); *C07D 209/08* (2013.01); *C07D 209/44* (2013.01)

(58) Field of Classification Search
USPC ........................................................ 514/751
See application file for complete search history.

(56) References Cited

U.S. PATENT DOCUMENTS

| | | |
|---|---|---|
| 4,010,282 A | 3/1977 | Binnig et al. |
| 2007/0015759 A1 | 1/2007 | Schulze et al. |

FOREIGN PATENT DOCUMENTS

| | | |
|---|---|---|
| FR | 2729146 A1 | 7/1996 |
| GB | 1307250 A | 2/1973 |
| JP | H02138162 A | 5/1990 |
| JP | H07188139 A | 7/1995 |
| WO | 9222279 A2 | 12/1992 |
| WO | 2004089470 A2 | 10/2004 |
| WO | 2004100865 A2 | 11/2004 |
| WO | 2009079624 A1 | 6/2009 |
| WO | 2012177618 A1 | 12/2012 |

OTHER PUBLICATIONS

The English translation of the Japanese Office Action, dated Feb. 18, 2019, in the related Japanese Appl. No. 2016-573483.
Examination Report, dated Feb. 26, 2019, in the related Australian Appl. No. 2015276256.
The English translation of the Chinese Search Report, dated Mar. 7, 2019, in the related Chinese Appl. No. 201580032317.6.
Fitzsimmons et al., "Synthesis and al Receptor Binding of Halogenated N,N'-Diphenethylethylenediamines," Med Chem (Los Angeles). 2011;1(102):1000102.
H. Bieraugel et al., "Models of folate coenzymes—VII : Synthesis and carbon transfer reactions of N5,N10-methenyl and N5,N10-methylenetetrahydrofolate models," Tetrahedron, V. 39, Issue 23, 1983, pp. 3971-3979.
Maso et al., "Ring Opening Reaction of 1,2-Diaryl-3-methyl-1,4,5,6-tetrahydropyrimidinium Salts with Metal Hydride Complexes," Journal of Heterocyclic Chemistry 31(1):25-31, Jan. 1994.

(Continued)

*Primary Examiner* — Kathrien A Cruz

(57) ABSTRACT

The present invention is directed to novel compounds of Formula (I), pharmaceutically acceptable salts or solvates thereof, and their use.

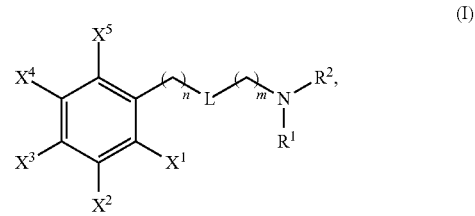

9 Claims, 3 Drawing Sheets

(56) References Cited

OTHER PUBLICATIONS

Figure 1:
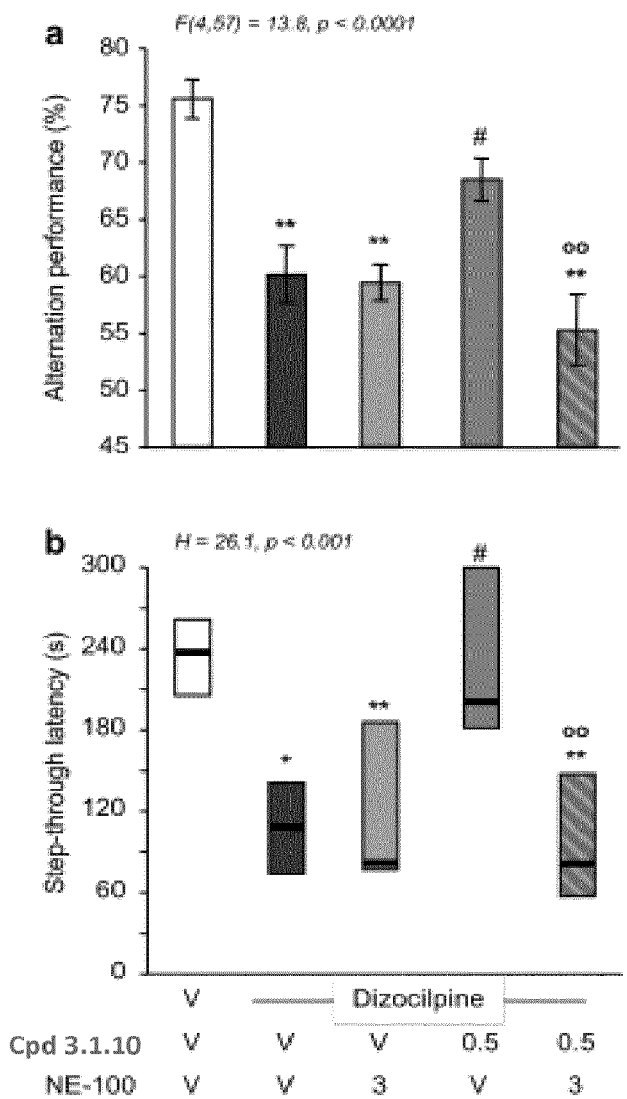

Van Duyne et al., "Effect of Mimetic CDK9 Inhibitors on HIV-1-Activated Transcription," J Mol Biol. Feb. 22, 2013; 425(4): 812-829.
CAS Registry No. 763096-57-7. STN Entry date: Oct. 15, 2004.
Fan et al., "Effect of structural modification in the amine portion of substituted aminobutyl-benzamides as ligands for binding r1 and r2 receptors," Bioorg Med Chem, Mar. 15, 2011;19(6):1852-9.
STN Registry Database, Aug. 21, 2006, (21 pages).
STN Registry Database, Aug. 21, 2006, (45 pages).

\* $p < 0.05$,
\*\* $p < 0.01$ vs (Vehicle (V) +Vehicle (V))-treated group,
$p < 0.05$ vs (Dizocilpine+V)-treated group,
oo $p < 0.01$ vs (Dizocilpine+ Compound 3.1.10)-treated group

COMPOUNDS, PHARMACEUTICAL COMPOSITION AND THEIR USE IN TREATING NEURODEGENERATIVE DISEASES

CROSS-REFERENCE TO RELATED APPLICATIONS

This application is a Divisional of U.S. patent application Ser. No. 15/317,742, filed Dec. 9, 2016, which is a National Stage Application of PCT/EP2015/063370 filed Jun. 15, 2015, which claims priority from European Patent Application No. 14305919.4 filed on Jun. 16, 2014. Each of the prior mentioned applications is hereby incorporated by reference herein in its entirety.

The present invention relates to novel compounds including their pharmaceutically acceptable salts and solvates, which are modulators, advantageously agonists of sigma-1 receptor (sigma-1, σ1R or Sig-1R) and are useful as therapeutic compounds, particularly in the treatment, prevention and/or diagnosis of neurodegenerative diseases.

BACKGROUND OF THE INVENTION

The sigma-1 receptor is an intracellular chaperone protein that resides specifically at the endoplasmic reticulum (ER)-mitochondrion interface, referred to as the mitochondrion-associated ER membrane (MAM). It is expressed in the central nervous system (CNS) in microglia, lymphocytes, neurons, and oligodendrocytes and is known to be implicated in the regulation of numerous neurotransmitters.

In the central nervous system (CNS), Sig-1Rs play a part in complex biological processes, which include cocaine or methamphetamine addiction, learning and memory, pain and depression. Some reports using the molecular biological silencing approach have implicated these receptors in neurodegenerative disorders such as Alzheimer's disease, stroke, and neural degeneration due to HIV infection.

Sig-1Rs are thus potential therapeutic targets in multiple CNS diseases and a variety of Sig-1R agonists and antagonists have been described.

Anavex 2-73 (1-(2,2-diphenyltetrahydrofuran-3-yl)-N,N-dimethylmethanamine hydrochloride) exhibits high affinity and selectivity to sigma-1 receptors and synergistic action with muscarinic and cholinergic receptors. Additional activities have been demonstrated on N-methyl-D-aspartate (NMDA) receptors. During in vitro and in vivo preclinical studies in mice, Anavex 2-73 demonstrated neuroprotective and anti-amnesic properties. Anavex 2-73 has been shown to provide protection from oxidative stress, which damages and destroys neurons and is believed to be a primary cause of Alzheimer's disease. Anavex 2-73 is currently under Phase I clinical trials.

Anavex 1-41 (1-(5,5-diphenyltetrahydrofuran-3-yl)-N,N-dimethylmethanamine hydrochloride) presents a mixed pharmacological activity involving the modulation of both sigma-1 and muscarinic components showing prominent anti-amnesic, anti-depressant at low sigma-1 agonistic doses. In addition, it presents mixed pharmacological activity involving the modulation of sodium and chloride channels.

Donepezil ((RS)-2-[(1-benzyl-4-piperidyl)methyl]-5,6-dimethoxy-2,3-dihydroinden-1-one) is an acetylcholine esterase inhibitor having non-selective sigma-1 agonistic activity. Donepezil is also an agonist of muscarinic and nicotinic receptors, and is a marketed drug used in the palliative treatment of Alzheimer's disease.

Other molecules having Sig-1R affinity are known but they either lack subtype selectivity over Sig-2R or they have high affinity for other receptors sites as do Anavex 1-41 and 2-73, and donepezil.

Drugs having poor selectivity (i.e. modulating the activity of multiple receptors) are more susceptible to inducing deleterious side effects, in particular to patients who are already under other medications.

There is therefore still a need for new selective modulators, especially agonists, of sigma-1 receptor activity of therapeutic value for the treatment and/or prevention of sigma-1 receptor related diseases, especially neurodegenerative diseases such as multiple sclerosis, Alzheimer's disease, Parkinson's disease, Huntington's disease, and Amyotrophic lateral sclerosis.

SUMMARY OF THE INVENTION

The invention encompasses compounds of general Formula I, their pharmaceutically acceptable salts and solvates as well as methods of use of such compounds or compositions comprising such compounds as modulators, especially agonists of sigma-1 receptor activity.

In a general aspect, the invention provides compounds of general Formula I:

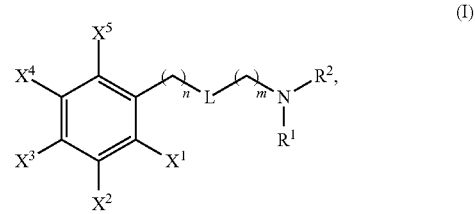

and pharmaceutically acceptable salts and solvates thereof, wherein $X^1$ and $X^5$ are independently selected from the group consisting of hydrogen, halogen, C1-C4-alkyl, C1-C4-haloalkyl, cyano, nitro, di(C1-C4-alkyl)amino, —NHCOOR', and —COOR', wherein R' is methyl, ethyl, n-propyl, n-butyl, iso-propyl, iso-butyl or tert-butyl;

$X^2$, $X^3$, $X^4$ are independently selected from the group consisting of hydrogen, chloro, C1-C4-alkyl, C1-C4-haloalkyl, C1-C4-alkoxy, cyano, nitro, di(C1-C4-alkyl)amino, —NHCOOR', and —COOR', wherein R' is methyl, ethyl, n-propyl, n-butyl, iso-propyl, iso-butyl or tert-butyl; with the proviso that at least one of $X^1$, $X^2$, $X^3$, $X^4$, $X^5$ is not hydrogen and that at least one of $X^2$, $X^3$, $X^4$ is not C1-C4-alkoxy;

L is —C(O)NH—, —NHC(O)—, —SO$_2$NH—, —NHSO$_2$—, or —NH—;

n is 0, 1 or 2;

m is 1, 2, 3, 4 or 5;

$R^1$ is H or alkyl, and $R^2$ is 5- or 6-membered arylalkyl, 5- or 6-membered cycloalkylalkyl, wherein the cyclic moiety of said arylalkyl or cycloalkylalkyl is optionally substituted by one or more substituents independently selected from halogen, preferably fluoro; or $R^1$ and $R^2$ form together with the nitrogen atom they are attached to a 5-membered heterocyclyl group, which is fused to a 5- or 6-membered aryl group and which is optionally substituted by one or more substituents independently selected from C1-C3 alkyl, preferably methyl, and wherein the resulting heterocyclic moiety is optionally substituted by one or more substituents independently selected from halogen, preferably fluoro.

In one embodiment, the compound of Formula I is not one, more or all of the following:

N-[3-[benzyl(methyl)amino]propyl]-4-chlorobenzamide;
N-[3-[benzyl(methyl)amino]propyl]benzamide;
N-[3-[benzyl(methyl)amino]propyl]-4-fluorobenzamide;
N-[3-[benzyl(methyl)amino]propyl]-4-bromobenzamide;
N-[3-[benzyl(methyl)amino]propyl]-4-methoxybenzamide;
N'-benzyl-N-[(4-chlorophenyl)methyl]-N'-methylpropane-1,3-diamine; and
N-[3-[benzyl(methyl)amino]propyl]-4-chlorobenzenesulfonamide.

In another aspect, the present invention provides a pharmaceutical composition comprising at least one compound according to the invention or a pharmaceutically acceptable salt or solvate thereof and at least one pharmaceutically acceptable carrier, diluent, excipient and/or adjuvant.

The invention also relates to the use of the above compounds or their pharmaceutically acceptable salts and solvates as modulators of sigma-1 receptor activity, preferably as agonists of sigma-1 receptors.

The invention further provides the use of a compound according to the invention or a pharmaceutically acceptable salt or solvate thereof as a medicament. Preferably, the medicament is used for the treatment and/or prevention of sigma-1 related diseases.

DETAILED DESCRIPTION OF THE INVENTION

As noted above, the invention relates to compounds of Formula I, as well as their pharmaceutically acceptable salts and solvates.

Preferred compounds of Formula I and pharmaceutically acceptable salts and solvates thereof are those wherein one or more of $X^1$, $X^2$, $X^3$, $X^4$, $X^5$, L, n, m, $R^1$, and $R^2$ are defined as follows:

$X^1$ and $X^5$ are independently selected from the group consisting of hydrogen, fluoro, chloro, bromo, iodo, C1-C4-alkyl, C1-C2-haloalkyl, cyano, nitro, and di(C1-C2-alkyl)amino, preferably $X^1$ and $X^5$ are independently selected from the group consisting of hydrogen, fluoro, chloro, bromo, C3-C4-alkyl, trifluoromethyl, cyano, nitro, and dimethylamino, more preferably $X^1$ and $X^5$ are independently selected from the group consisting of hydrogen, fluoro, chloro, n-propyl, n-butyl, t-butyl, trifluoromethyl, and dimethylamino, still more preferably $X^1$ and $X^5$ are independently selected from the group consisting of hydrogen, chloro, trifluoromethyl, and dimethylamino;

$X^2$, $X^3$, $X^4$ are independently selected from the group consisting of hydrogen, chloro, C1-C4-alkyl, C1-C2-haloalkyl, C1-C2-alkoxy, cyano, nitro, and di(C1-C2-alkyl)amino, preferably $X^2$, $X^3$, $X^4$ are independently selected from the group consisting of hydrogen, chloro, C3-C4-alkyl, trifluoromethyl, methoxy, cyano, nitro, and dimethylamino, more preferably $X^2$, $X^3$, $X^4$ are independently selected from the group consisting of hydrogen, chloro, n-propyl, n-butyl, t-butyl, trifluoromethyl, methoxy, and dimethylamino, still more preferably $X^1$, $X^2$, $X^3$, $X^4$, $X^5$ are independently selected from the group consisting of hydrogen, chloro, trifluoromethyl, and dimethylamino; always with the proviso that at least one of $X^1$, $X^2$, $X^3$, $X^4$, $X^5$ is not hydrogen and that at least one of $X^2$, $X^3$, $X^4$ is not C1-C2-alkoxy/methoxy;

n is 0 and L is selected from —C(O)NH—, —NHC(O)—, —SO$_2$NH—, preferably L is —C(O)NH—;
n is 1 and L is —NH— or —NHC(O)—;
m is 2, 3 or 4, preferably m is 2 or 3;
$R^1$ is H or C1-C4-alkyl, preferably $R^1$ is H or C1-C2 alkyl, more preferably $R^1$ is C1-C2 alkyl, still more preferably $R^1$ is methyl;
$R^2$ is 5- or 6-membered aryl-C1-C2-alkyl, 5- or 6-membered cycloalkyl-C1-C2-alkyl, wherein the cyclic moiety of said arylalkyl or cycloalkylalkyl group is optionally substituted by one or more substituents independently selected from halogen, preferably fluoro, preferably $R^2$ is benzyl, phenylethyl, or cyclohexylmethyl, wherein the cyclic moiety of each of said substituents is optionally substituted by one or more substituents independently selected from halogen, preferably fluoro, more preferably $R^2$ is benzyl or phenylethyl, wherein the cyclic moiety of each of said substituents is optionally substituted by one or more substituents independently selected from halogen, preferably fluoro, even more preferably $R^2$ is benzyl, optionally substituted by one or more substituents independently selected from halogen, preferably fluoro; advantageously $R^2$ is 5- or 6-membered aryl-C1-C2-alkyl, wherein the cyclic moiety of each of said substituents optionally substituted by one or more substituents independently selected from halogen, preferably fluoro, preferably $R^2$ is benzyl or phenylethyl, wherein the cyclic moiety of each of said substituents is optionally substituted by one or more substituents independently selected from halogen, preferably fluoro, more preferably $R^2$ is benzyl, optionally substituted by one or more substituents independently selected from halogen, preferably fluoro;
$R^1$ and $R^2$ form together with the nitrogen atom they are attached to a 5-membered heterocyclyl group, which is fused to a phenyl group and which is optionally substituted by one or more substituents independently selected from C1-C2 alkyl, preferably methyl, and wherein the resulting heterocyclic moiety is optionally substituted by one or more substituents independently selected from halogen, preferably fluoro, preferably $R^1$ and $R^2$ form together with the nitrogen atom they are attached to a isoindolinyl group optionally substituted by one or more substituents independently selected from C1-C2 alkyl, preferably methyl, and halogen, preferably fluoro.

Other preferred compounds of Formula I as defined above and pharmaceutically acceptable salts and solvates thereof are those wherein $X^1$, $X^2$, $X^3$, $X^4$, $X^5$ are as defined as follows:

$X^1$, $X^2$, $X^4$, $X^5$ are hydrogen and $X^3$ is chloro, C1-C4-alkyl, C1-C2-haloalkyl, C1-C2-alkoxy, cyano, nitro, or dialkylamino, preferably $X^3$ is chloro, C3-C4-alkyl, trifluoromethyl, methoxy, cyano, nitro, or dimethylamino, more preferably $X^3$ is chloro, n-propyl, n-butyl, i-butyl, trifluoromethyl or methoxy, more preferably $X^3$ is chloro, or trifluoromethyl, even more preferably $X^3$ is chloro;

$X^2$, $X^3$, $X^4$, $X^5$ are hydrogen and $X^1$ is fluoro, chloro, bromo, iodo, C1-C4-alkyl, C1-C2-haloalkyl, cyano, nitro, or dialkylamino, preferably $X^1$ is fluoro, chloro, bromo, C3-C4-alkyl, trifluoromethyl, cyano, nitro, or dimethylamino, more preferably $X^1$ is fluoro, chloro, bromo, n-propyl, n-butyl, t-butyl, trifluoromethyl, and dimethylamino, more preferably $X^1$ is chloro, bromo, trifluoromethyl, or dimethylamino, even more preferably $X^1$ is chloro or bromo;

$X^1$, $X^3$, $X^4$, $X^5$ are hydrogen and $X^2$ is chloro, C1-C4-alkyl, C1-C2-haloalkyl, C1-C2-alkoxy, cyano, nitro, or dialkylamino, preferably $X^2$ is chloro, C3-C4-alkyl, trifluoromethyl, methoxy, cyano, nitro, or dimethylamino, more preferably $X^2$ is chloro, n-propyl, n-butyl, t-butyl, trifluoromethyl, methoxy, and dimethylamino, more preferably $X^2$ is chloro, trifluoromethyl, methoxy, or dimethylamino, even more preferably $X^2$ is chloro, or dimethylamino;

$X^3$, $X^4$, and $X^5$ are hydrogen and $X^1$ and $X^2$ are independently selected from the group consisting of chloro, C1-C4-alkyl, C1-C2-haloalkyl, cyano, nitro, and dialkylamino, preferably $X^1$ and $X^2$ are independently selected from the group consisting of chloro, C3-C4-alkyl, trifluoromethyl, cyano, nitro, or dimethylamino, more preferably $X^1$ and $X^2$ are independently selected from the group consisting of chloro, n-propyl, n-butyl, t-butyl, trifluoromethyl, and dimethylamino, more preferably $X^1$ and $X^2$ are independently selected from the group consisting of chloro, trifluoromethyl, and dimethylamino, even more preferably $X^1$ and $X^2$ are both chloro;

$X^2$, $X^4$, and $X^5$ are hydrogen and $X^1$ and $X^3$ are independently selected from the group consisting of chloro, C1-C4-alkyl, C1-C2-haloalkyl, cyano, nitro, and dialkylamino, preferably $X^1$ and $X^3$ are independently selected from the group consisting of chloro, C3-C4-alkyl, trifluoromethyl, cyano, nitro, or dimethylamino, more preferably $X^1$ and $X^3$ are independently selected from the group consisting of chloro, n-propyl, n-butyl, t-butyl, trifluoromethyl, and dimethylamino, still more preferably $X^1$ and $X^3$ are independently selected from the group consisting of chloro, trifluoromethyl, and dimethylamino, even more preferably $X^1$ and $X^3$ are both chloro;

$X^1$, $X^4$, and $X^5$ are hydrogen and $X^2$ and $X^3$ are independently selected from the group consisting of chloro, C1-C4-alkyl, C1-C2-haloalkyl, C1-C2-alkoxy, cyano, nitro, and dialkylamino, preferably $X^2$ and $X^3$ are independently selected from the group consisting of chloro, C3-C4-alkyl, trifluoromethyl, methoxy, cyano, nitro, or dimethylamino, more preferably $X^2$ and $X^3$ are independently selected from the group consisting of chloro, n-propyl, n-butyl, t-butyl, trifluoromethyl, methoxy, and dimethylamino, more preferably $X^2$ and $X^3$ are independently selected from the group consisting of chloro, trifluoromethyl, and dimethylamino, even more preferably $X^2$ and $X^3$ are both chloro; or $X^1$, $X^3$, and $X^5$ are hydrogen and $X^2$ and $X^4$ are independently selected from the group consisting of chloro, C1-C4-alkyl, C1-C2-haloalkyl, C1-C2-alkoxy, cyano, nitro, and dialkylamino, preferably $X^2$ and $X^4$ are independently selected from the group consisting of chloro, C3-C4-alkyl, trifluoromethyl, methoxy, cyano, nitro, or dimethylamino, more preferably $X^2$ and $X^4$ are independently selected from the group consisting of chloro, n-propyl, n-butyl, t-butyl, trifluoromethyl, methoxy, and dimethylamino, more preferably $X^2$ and $X^4$ are independently selected from the group consisting of chloro, trifluoromethyl, and dimethylamino, even more preferably $X^2$ and $X^4$ are both chloro.

In one embodiment, preferred compounds of Formula I are those of Formula II:

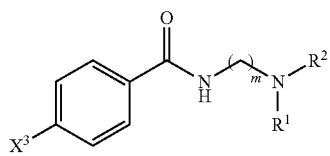

II and pharmaceutically acceptable salts and solvates thereof, wherein $X^3$, m, $R^1$, and $R^2$ are as defined above with respect to Formula I and any of its embodiments, with the proviso that $X^3$ is not hydrogen.

In one embodiment, the compounds of Formula II are those wherein $X^3$ is chloro, C1-C4-alkyl, C1-C2-haloalkyl, C1-C2-alkoxy, cyano, nitro, or dialkylamino, preferably $X^3$ is chloro, C3-C4-alkyl, trifluoromethyl, methoxy, cyano, nitro, or dimethylamino, more preferably $X^3$ is chloro, n-propyl, n-butyl, t-butyl, trifluoromethyl, methoxy, or dimethylamino, more preferably $X^3$ is chloro, trifluoromethyl, or dimethylamino, even more preferably $X^3$ is chloro, and/or m is 2, 3 or 4, preferably 2 or 3, and/or $R^1$ is methyl, and/or $R^2$ is benzyl optionally substituted by one or more substituents selected from the group consisting of halogen, preferably fluoro.

In one embodiment, preferred compounds of Formula I are those of Formula III:

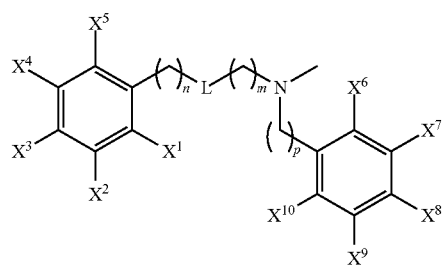

III and pharmaceutically acceptable salts and solvates thereof, wherein $X^1$, $X^2$, $X^3$, $X^4$, $X^5$, L, n and m are as defined above with respect to Formula I and any of its embodiments;

p is 1 or 2, preferably 1; and $X^6$, $X^7$, $X^8$, $X^9$, $X^{10}$ are independently selected from H, halogen preferably fluoro, preferably $X^6$, $X^7$, $X^8$, $X^9$, $X^{10}$ are all H.

In one embodiment, the compounds of Formula III are those of Formula III-a:

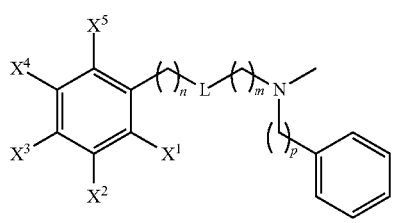

III-a and pharmaceutically acceptable salts and solvates thereof, wherein $X^1$, $X^2$, $X^3$, $X^4$, $X^5$, L, n, m and p are as defined above with respect to Formula III.

In one embodiment, the compounds of Formula III-a are those of Formula III-a-1:

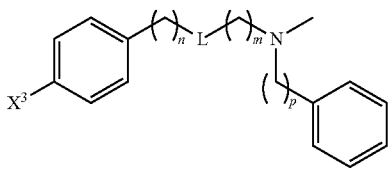

III-a-1 and pharmaceutically acceptable salts and solvates thereof, wherein
$X^3$ is chloro, C1-C4-alkyl, C1-C2-haloalkyl, C1-C2-alkoxy, cyano, nitro, or dialkylamino, preferably $X^3$ is chloro, C3-C4-alkyl, trifluoromethyl, methoxy, cyano, nitro, or dimethylamino, more preferably $X^3$ is chloro, n-propyl, n-butyl, t-butyl, trifluoromethyl, methoxy, or dimethylamino, more preferably $X^3$ is chloro, trifluoromethyl, or dimethylamino, even more preferably $X^3$ is chloro;
m is 1, 2, 3 or 4, preferably 1 or 3, more preferably 3; and/or
p is 1 or 2, preferably 1.

In one embodiment, the compounds of Formula III-a are those of Formula III-a-2:

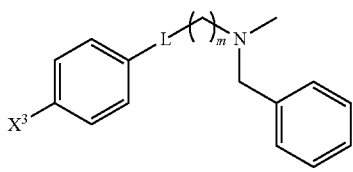

III-a-2 wherein
$X^3$ is chloro, C1-C4-alkyl, C1-C2-haloalkyl, C1-C2-alkoxy, cyano, nitro, or dialkylamino, preferably $X^3$ is chloro, C3-C4-alkyl, trifluoromethyl, methoxy, cyano, nitro, or dimethylamino, more preferably $X^3$ is chloro, n-propyl, n-butyl, t-butyl, trifluoromethyl, methoxy, or dimethylamino, more preferably $X^3$ is chloro, trifluoromethyl, or dimethylamino, even more preferably $X^3$ is chloro;
L is —NHC(O)— or —SO$_2$NH—; and/or
m is 2 or 3, preferably 3.

In one embodiment, the compounds of Formula III-a are those of Formula III-a-3:

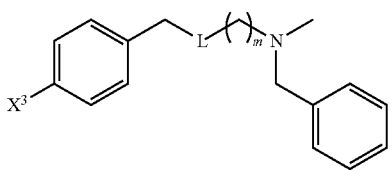

III-a-3 wherein
$X^3$ is chloro, C1-C4-alkyl, C1-C2-haloalkyl, C1-C2-alkoxy, cyano, nitro, or dialkylamino, preferably $X^3$ is chloro, C3-C4-alkyl, trifluoromethyl, methoxy, cyano, nitro, or dimethylamino, more preferably $X^3$ is chloro, n-propyl, n-butyl, t-butyl, trifluoromethyl, methoxy, or dimethylamino, more preferably $X^3$ is chloro, trifluoromethyl, or dimethylamino, even more preferably $X^3$ is chloro;
L is —NHC(O)— or —NH—; and/or
m is 1, 2 or 3, preferably 2 or 3.

Preferred compounds of Formula III-a-3 are those wherein L is —NHC(O)— and m is 2, or L is —NH— and m is 3.

In one embodiment, the compounds of Formula I are those of Formula IV:

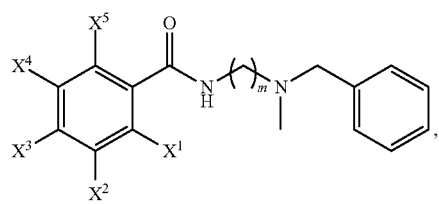

(IV)

wherein $X^1$, $X^2$, $X^3$, $X^4$, $X^5$, and m are as defined above with respect to Formula I and any of its embodiments.

Preferred compounds of formula IV are those of Formula IV-a:

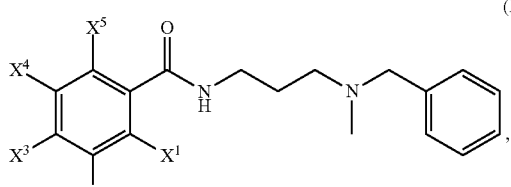

(IV-a)

wherein $X^1$, $X^2$, $X^3$, $X^4$, and $X^5$ are as defined above with respect to Formula IV.

Preferred compounds of formulae IV and IV-a are those wherein $X^1$, $X^2$, $X^3$, $X^4$, $X^5$ are independently selected from hydrogen, chloro, nitro, and trifluoromethyl; with the proviso that at least one of $X^1$, $X^2$, $X^3$, $X^4$, and $X^5$ is not hydrogen.

In one embodiment, the compounds of Formula I are those of Formula V:

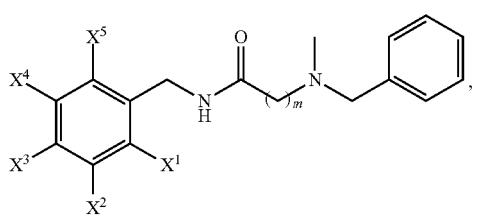

(V)

wherein $X^1$, $X^2$, $X^3$, $X^4$, $X^5$, and m are as defined above with respect to Formula I and any of its embodiments.

Preferred compounds of formula V are those of Formula V-a:

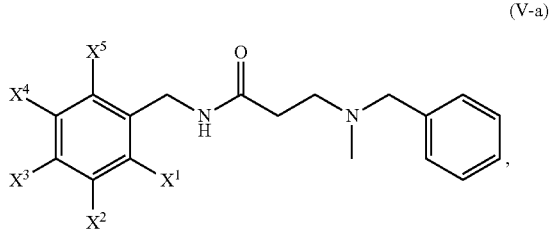

(V-a)

wherein $X^1$, $X^2$, $X^3$, $X^4$, and $X^5$ are as defined above with respect to Formula V.

Preferred compounds of formulae V and V-a are those wherein $X^1$, $X^2$, $X^3$, $X^4$, $X^5$ are independently selected from hydrogen, chloro, nitro, and trifluoromethyl; with the proviso that at least one of $X^1$, $X^2$, $X^3$, $X^4$, and $X^5$ is not hydrogen.

Particularly preferred compounds of the invention are those listed in Table 1 hereafter:

TABLE 1

| Cpd no. | Chemical name |
|---|---|
| 3.1.2 | N-[3-(benzylmethylamino)propyl]-4-propylbenzamide |
| 3.1.3 | N-[3-(benzylmethylamino)propyl]-4-butylbenzamide |
| 3.1.4 | N-[3-(benzylmethylamino)propyl]-4-tertbutylbenzamide |
| 3.1.5 | N-[3-(benzylmethylamino)propyl]-4-trifluoromethylbenzamide |
| 3.1.6 | N-[3-(benzylmethylamino)propyl]-4-fluorobenzamide |
| 3.1.7 | N-[3-(benzylmethylamino)propyl]-2-chlorobenzamide |
| 3.1.8 | N-[3-(benzylmethylamino)propyl]-3-chlorobenzamide |
| 3.1.9 | N-[3-(2-(N-methylbenzyl)amino)ethyl]-4-chlorobenzamide |
| 3.1.10 | N-[3-(benzylmethylamino)propyl]-4-chlorobenzamide |
| 3.1.11 | N-[4-(benzylmethylamino)butyl]-4-chlorobenzamide |
| 3.1.12 | N-[3-(N-methyl-2-phenylethylamino)propyl]-4-chlorobenzamide |
| 3.1.15 | N-[3-(isoindolin-2-yl)methylamino)propyl]-4-chlorobenzamide |
| 3.1.20 | N-[3-(benzylmethylamino)propyl]-2-bromobenzamide |
| 3.1.23 | N-[3-(benzylmethylamino)propyl]-2,3-dichlorobenzamide |
| 3.1.24 | N-[3-(benzylmethylamino)propyl]-2,4-dichlorobenzamide |
| 3.1.25 | N-[3-(benzylmethylamino)propyl]-3,4-dichlorobenzamide |
| 3.1.26 | N-[3-(benzylmethylamino)propyl]-3,5-dichlorobenzamide |
| 3.1.28 | N-[3-(benzylmethylamino)propyl]-3-methoxybenzamide |
| 3.1.29 | N-[3-(benzylmethylamino)propyl]-4-methoxybenzamide |
| 3.1.30 | N-[3-(benzylmethylamino)propyl]-3-dimethylaminobenzamide |
| 3.1.31 | N-[3-(benzylmethylamino)propyl]-4-cyanobenzamide |
| 3.1.32 | N-[3-(benzylmethylamino)propyl]-4-nitrobenzamide |
| 3.1.33 | N-(2-(benzyl(methyl)amino)ethyl)-3-chlorobenzamide |
| 3.1.34 | N-(2-(benzyl(methyl)amino)ethyl)-2,4-dichlorobenzamide |
| 3.1.36 | N-(2-(benzyl(methyl)amino)ethyl)-4-cyanobenzamide |
| 3.1.37 | N-(2-(benzyl(methyl)amino)ethyl)-4-nitrobenzamide |
| 3.2a | N-[3-(benzylmethylamino)propyl]-4-chlorobenzensulfonamide |
| 3.3a | 4-(benzylmethylamino)-N-(4-chlorophenyl)butanamide |
| 3.4a | N-(4-chlorobenzyl)-3-(benzylmethylamino)propanamide |
| 3.4b | N-(4-nitrobenzyl)-3-(benzylmethylamino)propanamide |
| 3.4c | N-(4-cyanobenzyl)-3-(benzylmethylamino)propanamide |
| 3.4d | N-(2,4-dichlorobenzyl)-3-(benzylmethylamino)propanamide |
| 3.4e | N-(3-chlorobenzyl)-3-(benzylmethylamino)propanamide |
| 3.5a | N-(4-chlorobenzyl)-3-(benzylmethylamino)propanamine |

The compounds of the invention can be prepared by different ways with reactions known by the person skilled in the art. Reaction schemes as described in the example section illustrate by way of example different possible approaches.

The compounds of the invention are indeed modulators, preferably agonists of sigma-1 receptor. They further have the advantage of being selective over the sigma-2 receptor. The invention thus also provides the use of the compounds of the invention or pharmaceutically acceptable salts, or solvates thereof as agonists of sigma-1 receptor.

Accordingly, in a particularly preferred embodiment, the invention relates to the use of compounds of Formula I and subformulae in particular those of Table 1 above, or pharmaceutically acceptable salts and solvates thereof, as sigma-1 agonists.

Applications

The compounds of the invention are therefore useful in the prevention and/or treatment of sigma-1 receptor related diseases or disorders.

The invention thus also relates to a compound of the invention or a pharmaceutically acceptable salt or solvate thereof for use in treating and/or preventing a sigma-1 receptor related disease or disorder. Or in other terms, the invention also relates to a method of treating and/or preventing a sigma-1 receptor related disease or disorder, comprising the administration of a therapeutically effective amount of a compound or pharmaceutically acceptable salt or solvate of the invention, to a patient in need thereof. Preferably the patient is a warm-blooded animal, more preferably a human.

Sigma-1 receptor related diseases or disorders within the meaning of the invention include, but are not limited to, neurodegenerative diseases, psychiatric disorders, drug addiction, pain and cancer.

Neurodegenerative diseases within the meaning of the present invention include, but are not limited to multiple sclerosis (MS), Parkinson's disease (PD), Huntington's disease (HD), Amyotrophic lateral sclerosis (ALS), stroke and dementia, the latter including, without being limited thereto, Alzheimer's disease (AD), vascular dementia, frontotemporal dementia, semantic dementia and dementia with Lewy bodies. Preferred neurodegenerative diseases are multiple sclerosis, Alzheimer's disease, Parkinson's disease, Huntington's disease, amyotrophic lateral sclerosis, and stroke. In a particular preferred embodiment the neurodegenerative disease is multiple sclerosis.

Psychiatric disorders within the meaning of the invention include, but are not limited to, schizophrenia, depression, and anxiety disorders, The invention further provides the use of a compound of the invention or a pharmaceutically acceptable salt or solvates thereof for the manufacture of a medicament for use in treating and/or preventing a sigma-1 receptor related disease or disorder. Preferably the patient is a warm-blooded animal, more preferably a human. The sigma-1 receptor related diseases or disorders are preferably those defined above.

According to a further feature of the present invention, there is provided a compound of the invention or a pharmaceutically acceptable salt or solvate for use in modulating sigma-1 receptor activity in a patient in need of such treatment, comprising administering to said patient an effective amount of a compound of the present invention, or a pharmaceutically acceptable salt or solvate thereof. In other terms, the invention also provides a method for modulating sigma-1 receptor activity, in a patient in need of such treatment, which comprises administering to said patient an effective amount of a compound of the present invention, or a pharmaceutically acceptable salt or solvate thereof. Preferably, the patient is a warm blooded animal, and even more preferably a human.

According to one embodiment, the compounds of the invention, their pharmaceutical acceptable salts or solvates may be administered as part of a combination therapy. Thus, are included within the scope of the present invention embodiments comprising coadministration of, and compositions and medicaments which contain, in addition to a compound of the present invention, a pharmaceutically acceptable salt or solvate thereof as active ingredient, additional therapeutic agents and/or active ingredients. Such multiple drug regimens, often referred to as combination therapy, may be used in the treatment and/or prevention of any sigma-1 receptor related disease or disorder, particularly those defined above.

Thus, the methods of treatment and pharmaceutical compositions of the present invention may employ the compounds of the invention or their pharmaceutical acceptable salts or solvates thereof in the form of monotherapy, but said methods and compositions may also be used in the form of multiple therapy in which one or more compounds of Formula I or their pharmaceutically acceptable salts or solvates are coadministered in combination with one or more other therapeutic agents.

The invention also provides pharmaceutical compositions comprising a compound of the invention or a pharmaceutically acceptable salt or solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt or solvate thereof as active ingredient, additional therapeutic agents and/or active ingredients.

Another object of this invention is a medicament comprising at least one compound of the invention, or a pharmaceutically acceptable salt or solvate thereof, as active ingredient.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), cerebral administration, for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

The compounds of the invention are also useful as diagnostic agents for diagnosing sigma-1 receptor related diseases or disorders. Sigma-1 receptor related diseases or disorders that may be diagnosed using the compounds, pharmaceutically acceptable salts or solvates of the invention are those described above.

The invention thus also relates to a compound of the invention or a pharmaceutically acceptable salt or solvate thereof for use in the diagnosis, especially the in vivo diagnosis of a sigma-1 receptor related disease or disorder.

In one embodiment, the diagnosis is an in vivo diagnosis performed by positron emission tomography (PET) or single-photon emission computed tomography (SPECT). The compounds of the invention or pharmaceutically acceptable salts or solvates thereof used in these methods are isotopically radiolabelled, preferably with an isotope selected from the group consisting of $^{11}C$, $^{13}N$, $^{15}O$, and $^{18}F$, more preferably with $^{18}F$.

In a variant of this embodiment, the compounds, pharmaceutically acceptable salts and solvates of the invention are those of Formula I and subformulae above, wherein the cyclic moiety of $R^2$ is optionally substituted by one or more substituents independently selected from radioactive halogen isotopes, preferably $^{18}F$ or wherein when $R^1$ and $R^2$ form together with the nitrogen atom they are attached to a 5- or 6-membered heterocyclyl group, which is optionally fused to a 5- or 6-membered aryl group and which is optionally substituted by one or more substituents independently selected from C1-C3 alkyl, preferably methyl, the resulting heterocyclic moiety is substituted by one or more substituents independently selected from radioactive halogen isotopes, preferably $^{18}F$.

The invention also provides a diagnostic composition, especially a diagnostic imaging composition, comprising a compound of the invention or a pharmaceutically acceptable salt or solvate thereof and at least one pharmaceutically acceptable carrier, diluent, excipient and/or adjuvant.

In one embodiment, the diagnostic composition is a diagnostic composition for positron emission tomography (PET) or single-photon emission computed tomography (SPECT). Compounds that are particularly useful in this embodiment are those described above with respect to the use of the compounds, pharmaceutically acceptable salts and solvates of the invention in the in vivo diagnosis performed by PET or SPECT.

Definitions

The definitions and explanations below are for the terms as used throughout the entire application, including both the specification and the claims.

Unless otherwise stated any reference to compounds of the invention herein, means the compounds as such as well as their pharmaceutically acceptable salts and solvates.

When describing the compounds of the invention, the terms used are to be construed in accordance with the following definitions, unless indicated otherwise.

The term "halo" or "halogen" means fluoro, chloro, bromo, or iodo. Preferred halo groups are fluoro and chloro, fluoro being particularly preferred.

The term "alkyl" by itself or as part of another substituent refers to a hydrocarbyl radical of Formula $C_nH_{2n+1}$ wherein n is a number greater than or equal to 1.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like. A preferred haloalkyl radical is trifluoromethyl.

The term "cycloalkyl" as used herein is a monovalent, saturated, or unsaturated monocyclic or bicyclic hydrocarbyl group. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, and cyclohexyl.

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows.

The term "aryl" as used herein refers to a polyunsaturated, aromatic hydrocarbyl group having a single ring (i.e. phenyl) or multiple aromatic rings fused together (e.g. naphtyl), typically containing 5 to 12 atoms; preferably 6 to 10, wherein at least one ring is aromatic.

The term "heteroaryl" as used herein by itself or as part of another group refers but is not limited to 5 to 12 carbon-atom aromatic rings or ring systems containing 1 to 2 rings which are fused together, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized.

The compounds of the invention containing a basic functional group may be in the form of pharmaceutically acceptable salts. Pharmaceutically acceptable salts of the compounds of the invention containing one or more basic functional groups include in particular the acid addition salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Pharmaceutically acceptable salts of compounds of Formulae I and subformulae may for example be prepared as follows:

(i) reacting the compound of Formula I or any of its subformulae with the desired acid; or (ii) converting one salt of the compound of Formula I or any of its subformulae to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The term "solvate" is used herein to describe a molecular complex comprising the compound of the invention and one or more pharmaceutically acceptable solvent molecules, for example, ethanol. The term 'hydrate' is employed when said solvent is water.

The compounds of the invention include compounds of the invention as hereinbefore defined, including all polymorphs and crystal habits thereof, prodrugs and isomers thereof (including optical, geometric and tautomeric isomers) and isotopically-labeled compounds of the invention.

In addition, although generally, with respect to the salts of the compounds of the invention, pharmaceutically acceptable salts are preferred, it should be noted that the invention in its broadest sense also includes non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of the invention.

The term "patient" refers to a warm-blooded animal, more preferably a human, who/which is awaiting or receiving medical care or is or will be the object of a medical procedure.

The term "human" refers to subjects of both genders and at any stage of development (i.e. neonate, infant, juvenile, adolescent, adult). In one embodiment, the human is an adolescent or adult, preferably an adult.

The terms "treat", "treating" and "treatment, as used herein, are meant to include alleviating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g. σ1R agonist) which is sufficient to achieve the desired therapeutic or prophylactic effect in the individual to which it is administered.

The term "administration", or a variant thereof (e.g., "administering"), means providing the active agent or active ingredient (e. g. σ1R agonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "agonist" as used herein means a ligand that activates an intracellular response when it binds to a receptor.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The present invention will be better understood with reference to the following examples and figures. These examples are intended to representative of specific embodiments of the invention, and are not intended as limiting the scope of the invention.

FIGURES

FIG. 1. Results of the spontaneous alternation (a) and passive avoidance assays (b) for compound 3.1.10.

Figure 2:
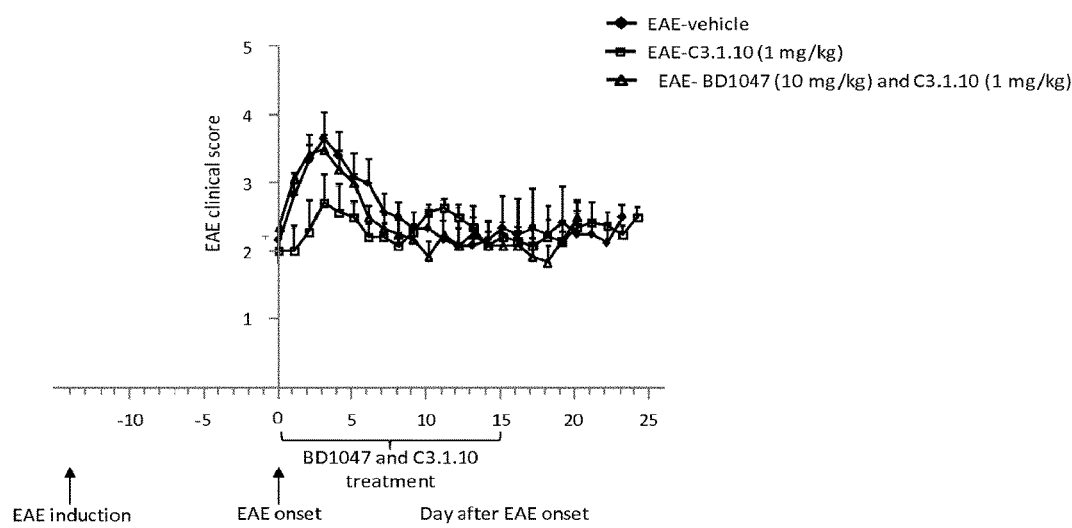

FIG. 2. Validation of σ1 action of compound 3.1.10. Data are presented as mean±sem.

Figure 3:
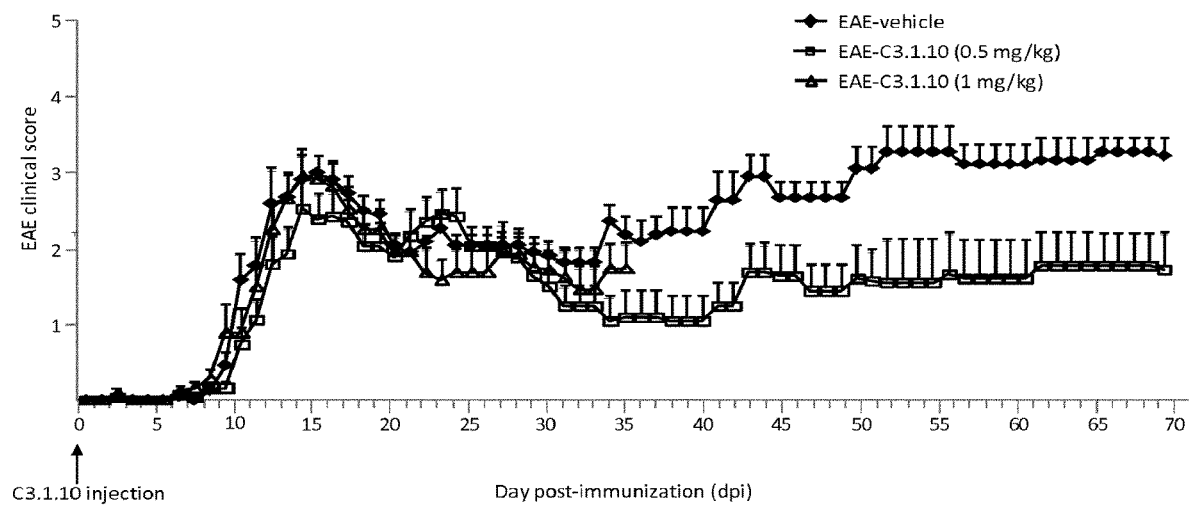

FIG. 3. Amelioration of EAE by compound 3.1.10, preventive treatment model. Data are presented as mean±sem.

Figure 4:
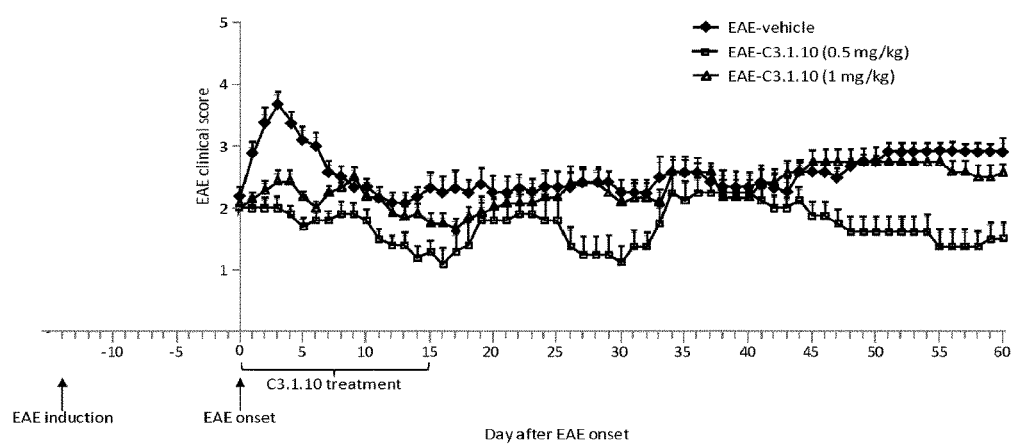

FIG. 4. Amelioration of EAE by compound 3.1.10, curative treatment model. Data are presented as mean±sem.

EXAMPLES

Chemistry Examples

All temperatures are expressed in ° C. and all reactions were carried out at room temperature (RT) unless otherwise stated.

$^1$H-, and $^{13}$C spectra were recorded on a 300 MHz Bruker spectrometer. Chemical shifts (δ) are given in ppm relative to the internal standard solvent. LC/MS chromatograms were recorded on a Waters Alliance 2695 system (X-Terra column, ionization mass spectrometer). For some compounds mass spectra were recorded on a MALDI-TOF Voyager-DE-STR (Applied Biosystems) apparatus.

Solvents, reagents and starting materials were purchased from well known chemical suppliers such as for example Sigma Aldrich, Acros Organics, Fluorochem, Eurisotop, VWR International, Sopachem and Polymer labs and the following abbreviations are used:
DCM: Dichloromethane,
DIEA: N,N-diisopropylethylamine,
DMF: N,N-dimethylformamide, EtOH: Ethanol,
MeOH: Methanol,
RT: Room temperature,
HOBt: Hydroxybenzotriazole,
HBtu: 2-(1H-benzotriazol-1-yl)-1,1,3,3-tetramethyluronium hexafluorophosphate,
LCMS: Liquid chromatography-mass spectrometry,
TLC: Thin layer chromatography,
MW: Molecular weight,
eq: Equivalent.

Scheme 1: Preparation of diamine intermediates

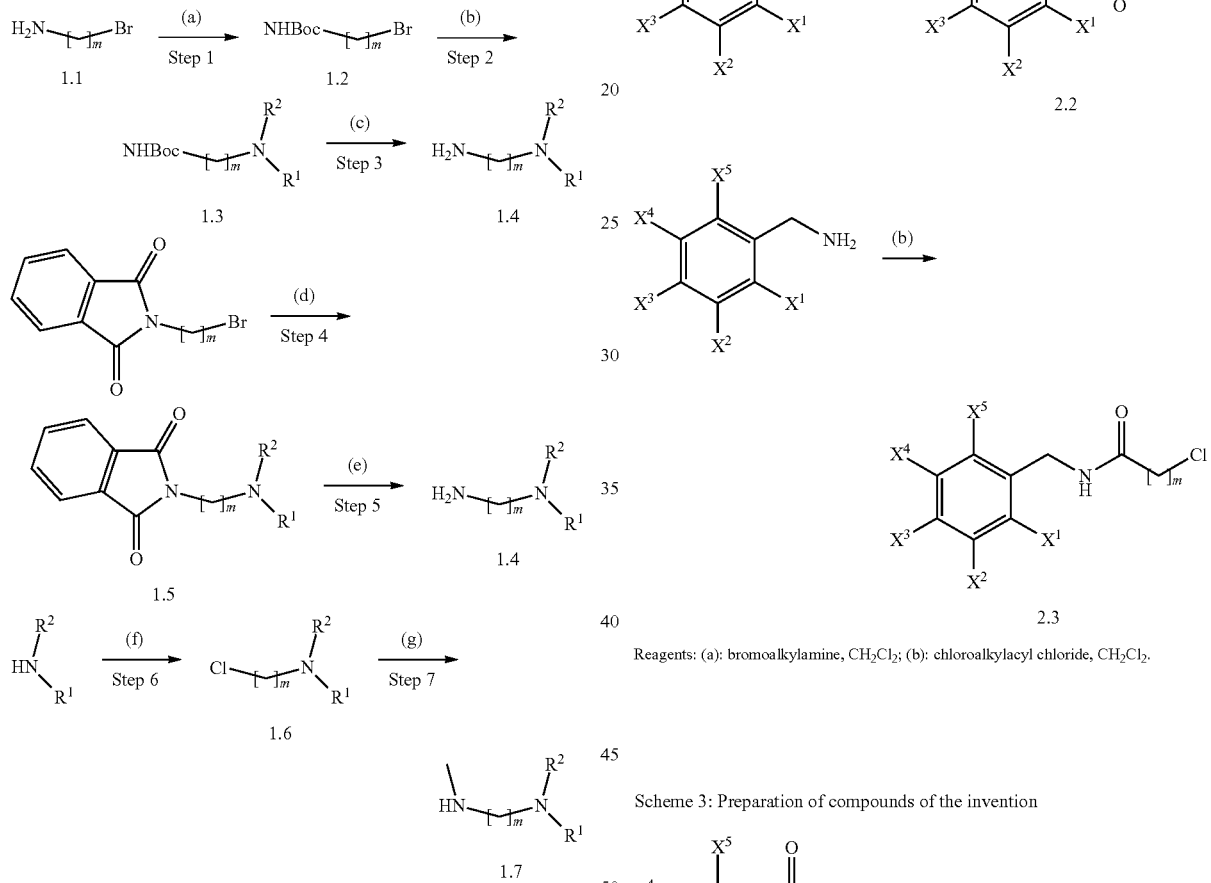

Reagents: (a): di-tert-butylcarbonate, triethylamine, CH$_2$Cl$_2$; (b): HNR$^1$R$^2$, potassium carbonate, DMF or CH$_3$CN; (c): 3M HCl in dry dioxane; (d): HNR$^1$R$^2$, potassium carbonate, DMF; (e) H$_2$NNH$_2$·H$_2$O, EtOH 96°; (f): bromochloroalkyl derivative, potassium carbonate, CH$_3$CN; (g): HNCH$_3$ 40%, potassium carbonate, CH$_3$CN.

Scheme 2: Preparation of aryl intermediates

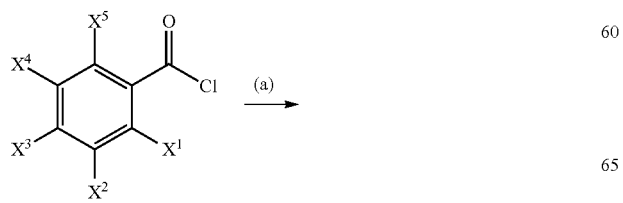

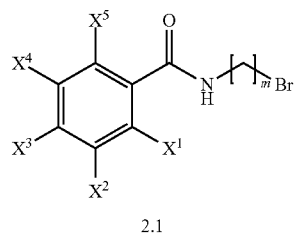

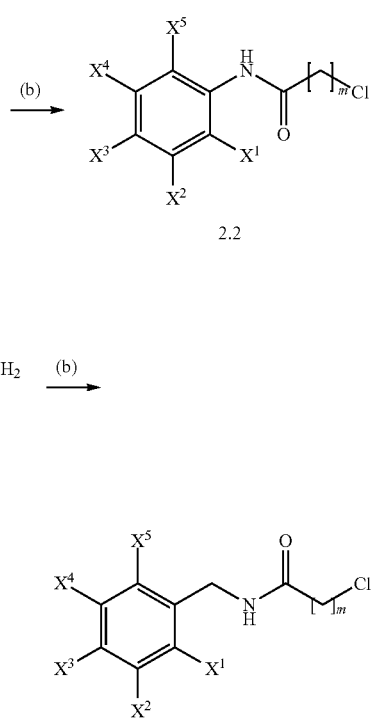

Reagents: (a): bromoalkylamine, CH$_2$Cl$_2$; (b): chloroalkylacyl chloride, CH$_2$Cl$_2$.

Scheme 3: Preparation of compounds of the invention

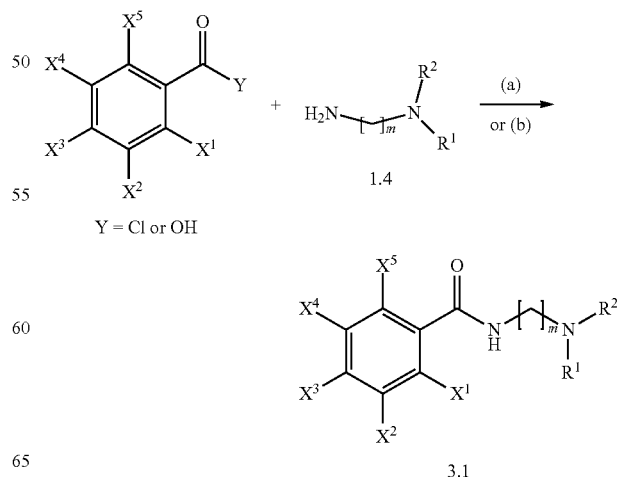

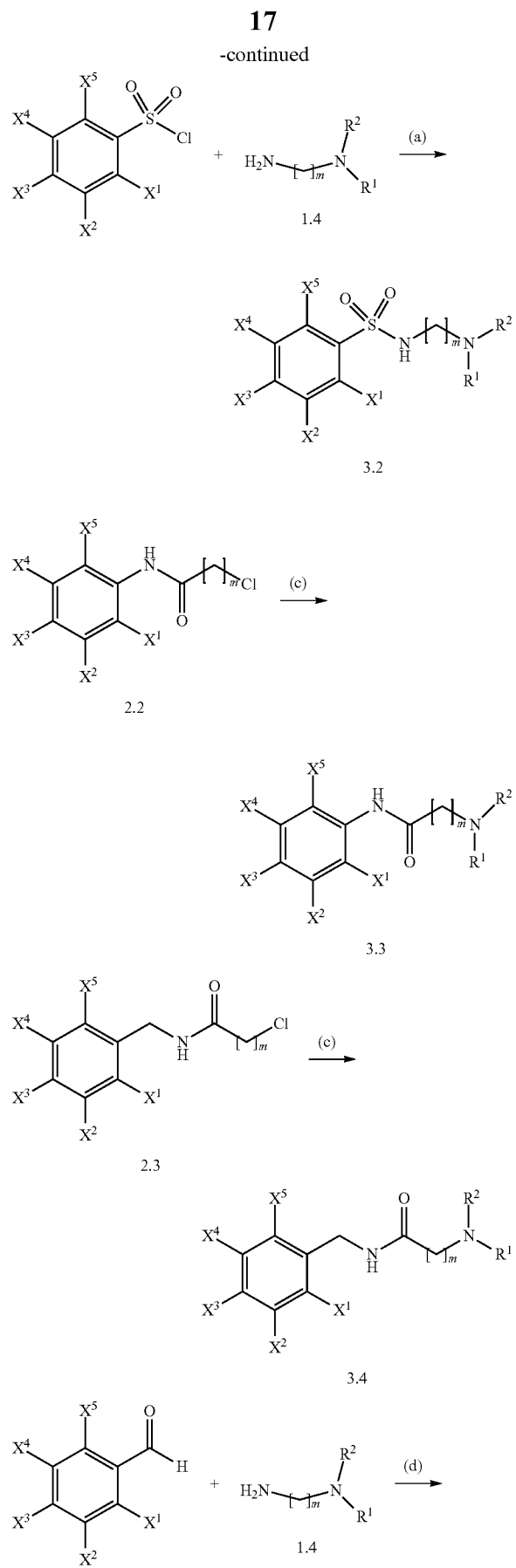

Reagents: (a): triethylamine, CH$_2$Cl$_2$ (Y = Cl), Procedure E1; (b): HOBt, HBtu, DIEA, CH$_2$Cl$_2$ (Y = OH), Procedure E2; (c): HNR$^1$R$^2$, Procedure E3 (d): NaBH$_4$, MeOH, Procedure E4.

2. Preparation of Diamine Intermediates (Compounds 1.4-1.7): Scheme 1

Step 1: Preparation of tert-butyl-3-bromopropylcarbamate (Compound 1.2)

3-Bromopropylamine (13.70 mmol, 3.0 g) was dissolved in 80 mL of dichloromethane. After addition of triethylamine (16.4 mmol, 2.32 mL) and di-tert-butylcarbonate (13.70 mmol, 3.0 g) the resulting mixture was stirred at room temperature overnight. Then, it was washed with 2×60 mL of a citric acid solution (5%) and 50 mL of saturated brine solution. The organic fraction was dried over magnesium sulphate and concentrated to give the desired product as yellow oil of sufficient purity for use without purification in the next step. Yield: 97%.

Step 2: Preparation of Compounds 1.3

To a mixture of tert-butyl-3-bromopropylcarbamate 1.2 (5.6 mmol, 1.3 eq, 1.3 g) and N,N-disubstituted amine (4.3 mmol, 1 eq) in 30 mL of DMF was added potassium carbonate (13.0 mmol, 3 eq, 1.8 g). The resulting mixture was heated at 70° C. for 24 hours. Then, the solvent was removed under reduced pressure and water (80 mL) added to the residue. The crude product was extracted with 3×60 mL of dichloromethane. The combined organic fractions were washed with 60 mL of water and dried over magnesium sulphate. The solvent was evaporated and the crude product collected as yellow oil. Purification by column chromatography (DCM:MeOH(NH$_3$), 9.7:0.3 (v/v)) was performed.

Example 1: Preparation of tert-butyl-3-[benzyl(methyl)amino]propyl carbamate (Compound 1.3a)

The compound 1.3a was synthesized according to the procedure by using tert-butyl-3-bromopropylcarbamate 1.2 (8.44 mmol, 2.0 g) and N-methylbenzylamine (6.50 mmol, 0.9 mL). Yield: 74%. LCMS m/z 279.1 [M+H]$^+$, 223.1 [M+H-tertBut]$^+$.

Example 2: Preparation of tert-butyl-3-[N-methyl-N-(2-phenylethyl)amino]propyl carbamate (Compound 1.3b)

The compound 1.3b was synthesized according to the procedure by using tert-butyl-3-bromopropylcarbamate 1.2 (8.44 mmol, 2.0 g) and N-methylphenylethylamine (6.50 mmol, 1.0 mL). Yield: 81%. LCMS (ESI$^+$-tertBut): 237.0.

Example 3: Preparation of tert-butyl-3-(isoindolin-2-yl)propylcarbamate (Compound 1.3c)

The compound 1.3c was synthesized according to the procedure by using tert-butyl-3-bromopropylcarbamate 1.2 (8.44 mmol, 2.0 g) and 2-isoindoline (6.50 mmol, 0.9 mL). Yield: 65%. LCMS m/z 221.0 [M+H-tertBut]$^+$.

Step 3: Preparation of Compounds 1.4

The compound 1.3 (1 eq) was dissolved in 72 mL of 3M HCl in dry 1,4-dioxane. The resulting mixture was stirred at room temperature overnight. Then, the solvent was removed under reduced pressure to give the desired product of sufficient purity for use without purification in the next step.

Example 1: Preparation of N$^1$-benzyl-N$^1$-methyl-propane-1,3-diamine dihydrochloride (Compound 1.4a)

The compound 1.4a was synthesized according to the procedure by using tert-butyl-3-[benzylmethylamino]propylcarbamate 1.3a (7.18 mmol, 1.8 g). Yield 98%. LCMS m/z 179.0 [M+H]$^+$.

Example 2: Preparation of N$^1$-benzyl-N$^1$-(2-phenylethyl)propane-1,3-diamine dihydrochloride (Compound 1.4b)

The compound 1.4b was synthesized according to the procedure by using tert-butyl-3-[N-methyl-N-(2-phenylethyl)amino]propylcarbamate 1.3b (7.18 mmol, 2.1 g). Yield: 88%. LCMS m/z 193.0 [M+H]$^+$

Example 3: Preparation of 3-(isoindolin-2-yl)propan-1-amine dihydrochloride (Compound 1.4c)

The compound 1.4c was synthesized according to the procedure by using tert-butyl-3-(isoindolin-2-yl)propylcarbamate 1.3c (7.18 mmol, 2.0 g). Yield: 83%. LCMS m/z 177.0 [M+H]$^+$.

Step 4: Preparation of Compounds 1.5

To a mixture of N-(bromoalkyl)phtalimide (1 eq) and N,N-disubstituted amine (1.2 eq) in 30 mL of DMF was added potassium carbonate (11.80 mmol, 2 eq, 1.6 g). The resulting mixture was heated at 90° C. for 16 hours. Then, inorganics were eliminated by filtration and the solvent was removed under reduced pressure. Purification by column chromatography (DCM:MeOH(NH$_3$), 9.9:0.1 (v/v)) was performed.

Example 1: Preparation of 2-[2-(benzylmethylamino)ethyl]-2,3-dihydro-1H-isoindole-1,3-dione (Compound 1.5a)

The compound 1.5a was synthesized according to the procedure by using N-(2-bromoethyl)phtalimide (5.9 mmol, 1.50 g) and N-methylbenzylamine (7.1 mmol, 0.9 mL). Yield 52%. LCMS m/z 295.0 [M+H]$^+$.

Example 2: Preparation of 2-[4-(benzylmethylamino)butyl]-2,3-dihydro-1H-isoindole-1,3-dion (Compound 1.5b)

The compound 1.5b was synthesized according to the procedure by using N-(4-bromobutyl)phtalimide (5.9 mmol, 1.66 g) and N-methylbenzylamine (7.1 mmol, 0.9 mL). Yield 53%. LCMS m/z 323.0 [M+H]$^+$.

Example 3: Preparation of 2-[2-(N-methyl-N-(2-phenylethyl)amino)ethyl]-2,3-dihydro-1H-isoindole-1,3-dione (Compound 1.5c)

The compound 1.5c was synthesized according to the procedure by using N-(2-bromoethyl)phtalimide (5.9 mmol, 1.50 g) and N-methyl-N-(2-phenylethyl)amine (7.1 mmol, 0.9 mL). Yield 64%. LCMS m/z 308.98 [M+H]$^+$.

Step 5: Preparation of Compounds 1.4

In 50 mL of ethanol 96°, was added a mixture of 2-[N,N-disubstitutedaminoalkyl]-2,3-dihydro-1H-isoindole-1,3-dione (1 eq) and hydrazine hydrate (10 eq). The resulting mixture was heated at reflux for 16 hours. The solution was removed under reduced pressure. The mineral was eliminated by filtration and washed with ethyl acetate. The filtrate was evaporated under reduced pressure to give an oily residue. Purification by column chromatography (DCM:MeOH(NH$_3$), 9:1 (v/v)) was performed. Oily purified product was dissolved in EtOAc and ether saturated with gazeous HCl was added. The corresponding hydrochloride product was filtered.

Example 1: Preparation of N$^1$-benzyl-N$^1$-methyl-ethane-1,2-diamine dihydrochloride (Compound 1.4d)

The compound 1.4d was synthesized according to the procedure by using 2-[2-(benzyl(methyl)amino)ethyl]-2,3-dihydro-1H-isoindole-1,3-dione (3.06 mmol, 0.9 g) and hydrazine hydrate (30.60 mmol, 1.5 mL). Yield 55%. LCMS m/z 165.0 [M+H]$^+$.

Example 2: Preparation of N$^1$-benzyl-N$^1$-methylbutane-1,4-diamine dihydrochloride (Compound 1.4e)

The compound 1.4e was synthesized according to the procedure by using 2-[4-(benzyl(methyl)amino)butyl]-2,3-dihydro-1H-isoindole-1,3-dione (6.2 mmol, 2.0 g) and hydrazine hydrate (62.0 mmol, 3.1 mL). Yield 73%. LCMS m/z 193.0 [M+H]$^+$.

Example 3: Preparation of N$^1$-(2-phenylethyl)-N$^1$-methylethane-1,2-diamine dihydrochloride (Compound 1.4f)

The compound 1.4f was synthesized according to the procedure by using 2-[2-(N-methyl-N-(2-phenylethyl)amino)ethyl]-2,3-dihydro-1H-isoindole-1,3-dione (3.06 mmol, 0.94 g) and hydrazine hydrate (30.60 mmol, 1.5 mL). Yield 67%. LCMS m/z 179.09 [M+H]$^+$.

Step 6: Preparation of Compounds 1.6

To a mixture of N,N-disubstitutedamine (1 eq) and bromochloroalkyl (1 eq) in 40 mL of DMF was added potassium carbonate (1 eq). The resulting mixture was stirred at room temperature for 1 day. Then, inorganics were eliminated by filtration and the solvent was removed under reduced pressure to give an oily residue. Purification by column chromatography (DCM:MeOH(NH$_3$), 9.8:0.2 (v/v)) was performed.

Example 1: Preparation of 3-chloropropyl-N-benzylmethylamine (1.6a)

The compound 1.6a was synthesized according to the procedure by using N-methylbenzylamine (33.0 mmol, 4.0 mL) and 1-bromo-3-chloropropane (33.0 mmol, 9.7 mL). Yield: 95%. LCMS m/z 196.0, 198.0 [M+H]$^+$.

Step 7: Preparation of Compounds 1.7

In 5 mL of CH$_3$CN was added a mixture of chloroalkyl-N,N-disubstitutedamine (1 eq) and methylamine 40% (20 eq). The resulting mixture was heated at reflux for 18 hours. The solution was removed under reduced pressure to give an oily residue. Purification by column chromatography (DCM:MeOH(NH$_3$), 9:1 (v/v)) was performed.

Example 1: Preparation of N$^1$-benzyl-N$^1$,N$^2$-dimethylpropane-1,3-diamine (Compound 1.7a)

The compound 1.7a was synthesized according to the procedure by using 3-chloropropyl-N-benzylmethylamine (10.1 mmol, 2.0 g) and methylamine 40% (202.0 mmol, 15.6 mL). Yield 88%. LCMS m/z 193.0 [M+H]$^+$.

3. Preparation of Intermediates Aryle Derivatives (Compounds 2.1-2.3): Scheme 2

Preparation of N-(3-bromopropyl)-4-chlorobenzamide (Compound 2.1)

To a solution of 3-bromopropylamine hydrobromide (2.86 mmol, 625 mg) in 10 mL of dichloromethane at 0° C. was added slowly a solution of 4-chlorobenzoyl chloride (2.86 mmol, 363 µL) in 5 mL of dichloromethane. The resulting mixture was stirred at room temperature for 12 hours. Then the solution was diluted with dichloromethane and washed successively with HCl (2M) solution, NaHCO$_3$ saturated solution and NaCl solution. The organic layer was dried over magnesium sulfate and evaporated. The crude product 2.1 was purified by column chromatography (DCM:cyclohexane, 5:5 (v/v)). Yield: 65%.

Preparation of 4-chloro-N-(4-chlorophenyl)butyramide (Compound 2.2)

To a solution of 4-chloroaniline (7.8 mmol, 1.0 g) in 15 mL of dichloromethane at 0° C. was added slowly a solution of 4-chlorobutyryl chloride (7.8 mmol, 878 µL) in 5 mL of dichloromethane. The resulting mixture was stirred at room temperature for 12 hours. Then the reaction was quenched with 25 mL of water and the product extract with 3×25 mL of DCM. The combined organic fractions were dried over magnesium sulphate and concentrated to give the desired product 2.2 with sufficient purity to be used without purification in the next step. Yield: 87%.

Preparation of Compounds 2.3

To a solution of substituted benzylamine (6.5 mmol, 1 eq) in AcOEt/H$_2$O (20 mL/15 mL), was added potassium carbonate (13.1 mmol, 1.8 g, 2 eq) and 3-chloropropionyl chloride (7.8 mmol, 753 µL). The resulting mixture was stirred at room temperature for 1 hour. The organic layer was washed successively with HCl (2M) solution (20 mL), water (20 mL) and dried over magnesium sulphate. The solution was removed under reduced pressure. The crude product 2.3 was washed with heptane and used in the next step.

Example 1: Preparation of N-(4-chlorobenzyl)-3-chloropropanamide (Compound 2.3a)

The compound 2.3.a was synthesized according to the procedure by using 4-chlorobenzylamine (6.5 mmol, 0.92 g). Yield: 60%. $^1$H NMR (300 MHz, CDCl$_3$), δ: 7.35-7.30 (m, 2H, H$_{aro}$); 7.25-7.20 (m, 2H, H$_{aro}$); 5.94 (br s, 1H, NH); 4.45 (d, J=6 Hz, 2H, CH$_2$); 3.84 (t, J=6 Hz, 2H, CH$_2$); 2.67 (t, J=6 Hz, 2H, CH$_2$).

Example 2: Preparation of N-(4-nitrobenzyl)-3-chloropropanamide (Compound 2.3b)

The compound 2.3.b was synthesized according to the procedure by using 4-nitrobenzylamine (6.5 mmol, 1.00 g). Yield: 69%. LCMS m/z 240.8 [M−H]$^-$.

Example 3: Preparation of N-(4-cyanobenzyl)-3-chloropropanamide (Compound 2.3c)

The compound 2.3.c was synthesized according to the procedure by using 4-cyanobenzylamine (6.5 mmol, 0.86 g). Yield: 65%. LCMS m/z 220.9 [M−H]$^-$.

Example 4: Preparation of N-(2,4-dichlorobenzyl)-3-chloropropanamide (Compound 2.3d)

The compound 2.3.d was synthesized according to the procedure by using 2,4-dichlorobenzylamine (6.5 mmol, 1.14 g). Yield: 79%. LCMS m/z 263.8, 265.8, 267.9 [M−H]$^-$.

Example 5: Preparation of N-(3-chlorobenzyl)-3-chloropropanamide (Compound 2.3e)

The compound 2.3.e was synthesized according to the procedure by using 3-chlorobenzylamine (6.5 mmol, 0.92 g). Yield: 73%. LCMS m/z 231.9, 233.9, 235.9 [M+H]$^+$.

Example 6: Preparation of N-(3-Bromobenzyl)-3-chloropropanamide (Compound 2.3f)

The compound 2.3.f was synthesized according to the procedure by using 3-bromobenzylamine (6.5 mmol, 1.21 g). Yield: 67%. LCMS m/z 275.8, 277.8, 279.8 [M+H]$^+$.

4. General Procedures E: Synthesis of Compounds of the Invention: Scheme 3

General Procedure E1:

A solution of N,N-disubstitutedalkyldiamine 1.4 (1 eq), and triethylamine (3 eq) in 10 mL of dichloromethane was cooled at 0° C. A solution of substituted-benzoylchloride (1 eq) in 5 mL of dichloromethane was added slowly. The resulting mixture was stirred at room temperature overnight. The solution was evaporated under reduced pressure. An aqueous solution of 3% sodium hydroxide (20 mL) was added and the mixture was stirred for 1 hour. The solution was extracted with dichloromethane. The organic fraction was dried over magnesium sulphate and concentrated to give an oily product. The residue was purified by thick layer chromatography or column chromatography.

General Procedure E2:

Reaction was carried out under nitrogen atmosphere. In 10 mL of dichloromethane, benzoic acid (1 eq), HOBt (1.2 eq) and HBtu (1.2 eq) were added and stirred at room temperature for 10 minutes. A solution of N,N-disubstituted-alkyldiamine 1.4 (1 eq) and DIEA (15 eq) in dichloromethane was added to the reacting mixture. After stirring at room temperature for 24 hours, the solvent was removed under reduced pressure and dichloromethane was added to the residue. The solution was washed with a solution of $NaHCO_3$ (5%) then saturated NaCl solution. The organic layer was dried over magnesium sulfate and evaporated under reduced pressure. The crude product was purified by thick layer chromatography or column chromatography.

General Procedure E3:

A solution of compound 2.2 or 2.3 (1 eq) in disubstitutedamine $HNR^1R^2$ (6 eq) was stirred at room temperature for 12 hours. A 5 mL amount of hexane was added and the white solid, identified as disubstitutedamine hydrochloride, was filtered. The filtrate was concentrated and purified by thick layer chromatography or column chromatography.

General Procedure E4:

A solution of substituted benzoylchloride (1 eq) and N,N-disubstitutedalkyldiamine 1.4 (1 eq) in MeOH (10 mL) was stirred at room temperature for 16 hours. Then, sodium borohydride (1.5 eq) was added and stirred for 3 hours. The mixture was quenched with water (5 mL) and evaporated under reduce pressure. The crude product was purified by thick layer chromatography or column chromatography.

Example 1: Synthesis of N-[3-(benzylmethylamino) propyl]-4-propylbenzamide (Compound 3.1.2)

The compound 3.1.2 was synthesized according to the procedure E1 by using $N^1$-benzyl-$N^1$-methylpropane-1,3-diamine dihydrochloride 1.4a (0.55 mmol, 138 mg), and 4-propylbenzoylchloride (0.55 mmol, 100 mg). Purification by column chromatography (DCM:MeOH($NH_3$), 9:1 (v/v)) was performed. Yield: 61%. $^1H$ NMR (300 MHz, $CDCl_3$), δ: 7.90 (br s, 1H, NH); 7.60 (d, J=8.2 Hz, 2H, $H_2$, $H_6$); 7.29-7.20 (m, 5H, $H_{aro}$); 7.13 (d, J=8.1 Hz, 2H, $H_3$, $H_5$); 3.55 (t, J=6.0 Hz, 2H, $CH_2$); 3.50 (s, 2H, $CH_2$); 2.60 (m, 4H, 2 $CH_2$); 2.23 (s, 3H, $CH_3$); 1.80 (p, J=6.0 Hz, 2H, $CH_2$); 1.62 (s, J=7.5 Hz, 2H, $CH_2$); 0.95 (t, J=7.3 Hz, 2H, $CH_3$). $^{13}C$ NMR (75 MHz, $CDCl_3$) δ: 167.2 (CO); 146.1 ($C_{aro}$); 138.4 ($C_{aro}$); 132.2 ($C_{aro}$); 129.3 ($C_{aro}$); 128.5 ($C_{aro}$); 128.4 ($C_{aro}$); 127.2 ($C_{aro}$); 126.9 ($C_{aro}$); 63.3 ($CH_2$); 57.1 ($CH_2$); 42.1 ($CH_3$); 40.2 ($CH_2$); 37.9 ($CH_2$); 25.5 ($CH_2$); 24.3 ($CH_2$); 14.2 ($CH_3$). LCMS m/z 325.0 $[M+H]^+$.

Example 2: Synthesis of N-[3-(benzylmethylamino) propyl]-4-butylbenzamide (Compound 3.1.3)

The compound 3.1.3 was synthesized according to the procedure E1 by using $N^1$-benzyl-$N^1$-methylpropane-1,3-diamine dihydrochloride 1.4a (0.65 mmol, 163 mg), and 4-butylbenzoylchloride (0.65 mmol, 100 mg). Purification by column chromatography (DCM:MeOH($NH_3$), 9:1 (v/v)) was performed. Yield: 30%. $^1H$ NMR (300 MHz, $CDCl_3$), δ: 7.97 (br s, 1H, NH); 7.60 (d, 0.1=8.2 Hz, 2H, $H_2$, $H_6$); 7.29-7.23 (m, 5H, $H_{aro}$); 7.13 (d, J=8.2 Hz, 2H, $H_3$, $H_5$); 3.56 (m, 4H, $2CH_2$); 2.64 (m, 4H, $2CH_2$); 2.28 (s, 3H, $CH_3$); 1.83 (p, J=6.1 Hz, 2H, $CH_2$); 1.62 (m, 2H, $CH_2$); 1.35 (m, 2H, $CH_2$); 0.97 (t, J=7.1 Hz, 2H, $CH_3$). $^{13}C$ NMR (75 MHz, $CDCl_3$) δ: 167.7 (CO); 146.7 ($C_{aro}$); 138.0 ($C_{aro}$); 132.5 ($C_{aro}$); 129.8 (2 $C_{aro}$); 128.8 (4 $C_{aro}$); 127.9 ($C_{aro}$); 127.3 (2 $C_{aro}$); 63.5 ($CH_2$); 57.1 ($CH_2$); 41.9 ($CH_3$); 40.3 ($CH_2$); 35.9 ($CH_2$); 33.7 ($CH_2$); 25.7 ($CH_2$); 22.6 ($CH_2$); 14.3 ($CH_3$). LCMS m/z 339.0 $[M+H]^+$.

Example 3: Synthesis of N-[3-(benzylmethylamino) propyl]-4-tert-butylbenzamide (Compound 3.1.4)

The compound 3.1.4 was synthesized according to the procedure E1 by using $N_1$-benzyl-$N^1$-methylpropane-1,3-diamine dihydrochloride 1.4a (0.60 mmol, 150 mg), and 4-tertbutylbenzoylchloride (0.60 mmol, 100 mg). Purification by column chromatography (DCM:MeOH($NH_3$), 9:1 (v/v)) was performed. Yield: 27%. $^1H$ NMR (300 MHz, $CDCl_3$), δ: 8.03 (br s, 1H, NH); 7.63 (d, J=8.5 Hz, 2H, $H_2$, $H_6$); 7.37 (d, J=8.5 Hz, 2H, $H_3$, $H_5$); 7.29-7.24 (m, 5H, $H_{aro}$); 3.57 (m, 4H, $2CH_2$); 2.63 (t, J=6.0 Hz, 2H, $CH_2$); 2.28 (s, 3H, $NCH_3$); 1.84 (p, J=5.9 Hz, 2H, $CH_2$); 1.32 (s, 9H, $3CH_3$). $^{13}C$ NMR (75 MHz, $CDCl_3$) δ: 167.1 (CO); 154.4 ($C_{aro}$); 137.8 ($C_{aro}$); 131.8 ($C_{aro}$); 129.5 (2 $C_{aro}$); 128.4 (2 $C_{aro}$); 127.4 ($C_{aro}$); 126.8 (2 $C_{aro}$); 125.3 (2 $C_{aro}$); 63.1 ($CH_2$); 56.9 ($CH_2$); 41.5 ($CH_3$); 40.1 ($CH_2$); 34.8 (C); 31.2 ($CH_3$); 25.3 ($CH_2$). LCMS m/z 339.0 $[M+H]^+$.

Example 4: Synthesis of N-[3-(benzylmethylamino) propyl]-4-trifluoromethylbenzamide (Compound 3.1.5)

The compound 3.1.5 was synthesized according to the procedure E1 by using $N^1$-benzyl-$N^1$-methylpropane-1,3-diamine dihydrochloride 1.4a (0.48 mmol, 120 mg), and 4-trifluoromethylbenzoylchloride (0.48 mmol, 100 mg). Purification by column chromatography (DCM:MeOH ($NH_3$), 9:1 (v/v)) was performed. Yield: 57%. $^1H$ NMR (300 MHz, $CDCl_3$), δ: 8.50 (br s, 1H, NH); 7.78 (d, J=8.2 Hz, 2H, $H_2$, $H_6$); 7.59 (d, J=8.2 Hz, 2H, $H_3$, $H_5$); 7.28-7.21 (m, 5H, $H_{aro}$); 3.63-3.55 (m, 4H, 2 $CH_2$); 2.68 (t, J=5.8 Hz, 2H, $CH_2$); 2.30 (s, 3H, $CH_3$); 1.85 (p, J=5.7 Hz, 2H, $CH_2$). $^{13}C$ NMR (75 MHz, $CDCl_3$) δ: 165.8 (CO); 138.0 ($C_{aro}$); 129.5 (2 $C_{aro}$); 128.5 (2 $C_{aro}$); 127.7 ($C_{aro}$); 127.4 (2 $C_{aro}$); 125.5 (2 $C_{aro}$); 125.4 (2 $C_{aro}$); 62.9 ($CH_2$); 57.1 ($CH_2$); 41.3 ($CH_3$); 40.5 ($CH_2$); 24.8 ($CH_2$). LCMS m/z 351.0, 352.0 $[M+H]^+$.

Example 5: Synthesis of N-[3-(benzylmethylamino) propyl]-4-fluorobenzamide (Compound 3.1.6)

The compound 3.1.6 was synthesized according to the procedure E2 by using $N^1$-benzyl-$N^1$-methylpropane-1,3-diamine dihydrochloride 1.4a (0.67 mmol, 170 mg), and 4-fluorobenzoic acid (0.67 mmol, 90 mg). Purification by thick layer chromatography (DCM:MeOH($NH_3$), 9:1 (v/v)) was performed. Yield: 58%. $^1H$ NMR (300 MHz, $CDCl_3$), δ: 8.20 (br s, 1H, NH); 7.66 (m, 2H, $H_2$, $H_6$); 7.28-7.24 (m, 5H, $H_{aro}$); 7.00 (t, J=9.1 Hz, 2H, $H_3$, $H_5$); 3.60-3.52 (m, 4H, 2 $CH_2$); 2.65 (t, J=6.1 Hz, 2H, $CH_2$); 2.28 (s, 3H, $CH_3$); 1.83 (p, J=6.0 Hz, 2H, $CH_2$). $^{13}C$ NMR (75 MHz, $CDCl_3$) δ: 166.1 (CO); 164.5 ($C_{aro}$); 137.6 ($C_{aro}$); 130.8 ($C_{aro}$); 129.5 (2 $C_{aro}$); 129.2 (2 $C_{aro}$); 128.5 (2 $C_{aro}$); 127.6 ($C_{aro}$); 115.3 (2 $C_{aro}$); 63.1 ($CH_2$); 57.1 ($CH_2$); 41.4 ($CH_3$); 40.3 ($CH_2$); 25.0 ($CH_2$). LCMS m/z 301.1, 302.1 $[M+H]^+$.

Example 6: Synthesis of N-[3-(benzylmethylamino) propyl]-2-chlorobenzamide (Compound 3.1.7)

The compound 3.1.7 was synthesized according to the procedure E1 by using $N^1$-benzyl-$N^1$-methylpropane-1,3- diamine dihydrochloride 1.4a (0.57 mmol, 143 mg), and 2-chlorobenzoylchloride (0.57 mmol, 100 mg). Purification by column chromatography (DCM:MeOH(NH$_3$), 9:1 (v/v)) was performed. Yield: 46%. $^1$H NMR (300 MHz, CDCl$_3$), δ: 7.52 (dd, J=7.0 Hz, J=1.9 Hz, 1H, H$_6$); 7.39-7.25 (m, 4H, NH, H$_3$, H$_4$, H$_5$); 7.17-7.09 (m, 5H, H$_{aro}$); 3.54 (q, J=6.2 Hz, 2H, CH$_2$); 3.49 (s, 2H, CH$_2$); 2.58 (t, J=6.3 Hz, 2H, CH$_2$); 2.21 (s, 3H, NCH$_3$); 1.83 (p, J=6.2 Hz, 2H, CH$_2$). $^{13}$C NMR (75 MHz, CDCl$_3$) δ: 166.7 (CO); 137.9 (C$_{aro}$); 136.0 (C$_{aro}$); 130.8 (C$_{aro}$); 130.7 (C$_{aro}$); 130.1 (C$_{aro}$); 129.5 (C$_{aro}$); 128.9 (2 C$_{aro}$); 128.3 (2 C$_{aro}$); 127.2 (C$_{aro}$); 126.9 (C$_{aro}$); 62.6 (CH$_2$); 56.0 (CH$_2$); 41.8 (CH$_3$); 39.7 (CH$_2$); 25.3 (CH$_2$). LCMS m/z 317.0, 319.0 [M+H]$^+$.

Example 7: Synthesis of N-[3-(benzylmethylamino)propyl]-3-chlorobenzamide (Compound 3.1.8)

The compound 3.1.8 was synthesized according to the procedure E1 by using N$^1$-benzyl-N$^1$-methylpropane-1,3-diamine dihydrochloride 1.4a (0.57 mmol, 143 mg), and 3-chlorobenzoylchloride (0.57 mmol, 100 mg). Purification by column chromatography (DCM:MeOH(NH$_3$), 9:1 (v/v)) was performed. Yield: 8%. $^1$H NMR (300 MHz, CDCl$_3$), δ: 8.22 (br s, 1H, NH); 7.78 (dd, J=1.5 Hz, J=2.0 Hz, 1H, H$_2$); 7.68 (d, J=8.0 Hz, 1H, H$_6$); 7.52 (d, J=7.8 Hz, 1H, H$_4$); 7.52 (t, J=7.3 Hz, 1H, H$_5$); 7.32-7.22 (m, 5H, H$_{aro}$); 3.58-3.51 (m, 4H, 2CH$_2$); 2.63 (t, J=7.5 Hz, 2H, CH$_2$); 2.30 (s, 3H, CH$_3$); 1.84 (p, J=6.4 Hz, 2H, CH$_2$). $^{13}$C NMR (75 MHz, CDCl$_3$) δ: 165.8 (CO); 136.5 (C$_{aro}$); 134.6 (C$_{aro}$); 131.2 (C$_{aro}$); 129.7 (C$_{aro}$); 129.4 (2 C$_{aro}$); 128.5 (2 C$_{aro}$); 127.7 (2 C$_{aro}$); 127.5 (C$_{aro}$); 125.0 (C$_{aro}$); 63.1 (CH$_2$); 56.7 (CH$_2$); 41.6 (CH$_3$); 40.4 (CH$_2$); 24.8 (CH$_2$). LCMS m/z 317.0, 319.0 [M+H]$^+$.

Example 8: Synthesis of N-[3-(2-(N-methylbenzyl)amino)ethyl]-4-chlorobenzamide (Compound 3.1.9)

The compound 3.1.9 was synthesized according to the procedure E1 by using N$^1$-benzyl-N$^1$-methylethane-1,2-diamine dihydrochloride 1.4d (0.57 mmol, 135 mg), and 4-chlorobenzoylchloride (0.57 mmol, 100 mg). Purification by column chromatography (DCM:MeOH(NH$_3$), 9:1 (v/v)) was performed. Yield: 20%. $^1$H NMR (300 MHz, CDCl$_3$), δ: 7.67 (d, J=8.6 Hz, 2H, H$_2$, H$_6$); 7.41 (d, J=8.6 Hz, 2H, H$_3$, H$_5$); 7.23-7.33 (m, 5H, H$_{aro}$); 6.78 (br s, 1H, NH); 3.56 (s, 2H, CH$_2$); 3.51 (q, J=5.2 Hz, 2H, CH$_2$); 2.62 (t, J=5.9 Hz, 2H, CH$_2$); 2.31 (s, 3H, NCH$_3$). $^{13}$C NMR (75 MHz, CDCl$_3$) δ: 166.4 (CO); 138.6 (C$_{aro}$); 137.5 (C$_{aro}$); 133.1 (C$_{aro}$); 129.4 (2 C$_{aro}$); 129.1 (2 C$_{aro}$); 128.9 (2 C$_{aro}$); 128.7 (2 C$_{aro}$); 127.4 (C$_{aro}$); 62.3 (CH$_2$); 54.9 (CH$_2$); 42.1 (CH$_3$); 37.1 (CH$_2$). LCMS m/z 303.0, 305.0 [M+H]$^+$.

Example 9: Synthesis of N-[3-(benzylmethylamino)propyl]-4-chlorobenzamide (Compound 3.1.10)

The compound 3.1.10 was synthesized according to the procedure E1 by using N$^1$-benzyl-N$^1$-methylpropane-1,3-diamine dihydrochloride 1.4a (0.57 mmol, 143 mg), and 4-chlorobenzoylchloride (0.57 mmol, 100 mg). Purification by column chromatography (DCM:MeOH(NH$_3$), 9:1 (v/v)) was performed. Yield: 55%. $^1$H NMR (300 MHz, CDCl$_3$), δ: 8.25 (br s, 1H, NH); 7.60 (d, J=9 Hz, 2H, H$_2$, H$_6$); 7.33-7.21 (m, 7H, H$_3$, H$_5$, H$_{aro}$); 3.62-3.51 (m, 4H, 2CH$_2$); 2.65 (t, J=5.4 Hz, 2H, CH$_2$); 2.27 (s, 3H, NCH$_3$); 1.83 (p, J=5.5 Hz, 2H, CH$_2$). $^{13}$C NMR (75 MHz, CDCl$_3$) δ: 166.0 (CO); 137.8 (C$_{aro}$); 137.3 (C$_{aro}$); 133.1 (C$_{aro}$); 129.4 (2 C$_{aro}$); 128.6 (2 C$_{aro}$); 128.5 (2 C$_{aro}$); 128.4 (2 C$_{aro}$); 127.5 (C$_{aro}$); 63.2 (CH$_2$); 57.2 (CH$_2$); 41.5 (CH$_3$); 40.5 (CH$_2$); 25.0 (CH$_2$). LCMS m/z 316.9, 318.9 [M+H]$^+$.

Example 10: Synthesis of N-[4-(benzylmethylamino)butyl]-4-chlorobenzamide (Compound 3.1.11)

The compound 3.1.11 was synthesized according to the procedure E1 by using N$^1$-benzyl-N$^1$-methylbutane-1,4-diamine dihydrochloride 1.4e (0.57 mmol, 151 mg), and 4-chlorobenzoylchloride (0.57 mmol, 100 mg). Purification by column chromatography (DCM:MeOH(NH$_3$), 9:1 (v/v)) was performed. Yield: 25%. $^1$H NMR (300 MHz, CDCl$_3$), δ: 7.60 (d, J=9.2 Hz, 2H, H$_2$, H$_6$); 7.41 (br s, 1H, NH); 7.33-7.26 (m, 7H, H$_3$, H$_5$, H$_{aro}$); 3.53 (s, 2H, CH$_2$); 3.45 (q, J=6.2 Hz, 2H, CH$_2$); 2.45 (t, J=6.4 Hz, 2H, CH$_2$); 2.17 (s, 3H, NCH$_3$); 1.73-1.62 (m, 4H, 2CH$_2$). $^{13}$C NMR (75 MHz, CDCl$_3$) δ: 166.6 (CO); 137.7 (C$_{aro}$); 137.3 (C$_{aro}$); 133.3 (C$_{aro}$); 129.3 (2 C$_{aro}$); 128.6 (2 C$_{aro}$); 128.5 (2 C$_{aro}$); 128.4 (2 C$_{aro}$); 127.4 (C$_{aro}$); 61.8 (CH$_2$); 56.7 (CH$_2$); 42.1 (CH$_3$); 39.9 (CH$_2$); 27.1 (CH$_2$); 24.8 (CH$_2$). LCMS m/z 331.0, 333.0 [M+H]$^+$.

Example 11: Synthesis of N-[3-(N-methyl-2-phenylethylamino)propyl]-4-chlorobenzamide (Compound 3.1.12)

The compound 3.1.12 was synthesized according to the procedure E1 by using N$^1$-benzyl-N$^1$-(2-phenylethyl)propane-1,3-diamine dihydrochloride 1.4b (0.57 mmol, 151 mg), and 4-chlorobenzoylchloride (0.57 mmol, 100 mg). Purification by column chromatography (DCM:MeOH(NH$_3$), 9:1 (v/v)) was performed. Yield: 69%. $^1$H NMR (300 MHz, CDCl$_3$), δ: 8.25 (br s, 1H, NH); 7.58 (d, J=8.3 Hz, 2H, H$_2$, H$_6$); 7.34 (d, J=8.4 Hz, 2H, H$_3$, H$_5$); 7.26-7.12 (m, 5H, H$_{aro}$); 3.53 (q, J=6.2 Hz, 2H, CH$_2$); 2.82 (m, 2H, CH$_2$); 2.75 (m, 2H, CH$_2$); 2.66 (t, J=6.0 Hz, 2H, CH$_2$); 2.35 (s, 3H, NCH$_3$); 1.80 (p, J=5.9 Hz, 2H, CH$_2$). $^{13}$C NMR (75 MHz, CDCl$_3$) δ: 165.9 (CO); 139.5 (C$_{aro}$); 137.2 (C$_{aro}$); 133.1 (C$_{aro}$); 128.6 (4 C$_{aro}$); 128.5 (2 C$_{aro}$); 128.3 (2 C$_{aro}$); 126.3 (C$_{aro}$); 59.6 (CH$_2$); 57.1 (CH$_2$); 41.7 (CH$_3$); 40.4 (CH$_2$); 33.3 (CH$_2$); 24.3 (CH$_2$). LCMS m/z 331.0, 333.0 [M+H]$^+$.

Example 12: Synthesis of N-[3-(isoindolin-2-yl)methylamino)propyl]-4-chlorobenzamide (Compound 3.1.15)

The compound 3.1.15 was synthesized according to the procedure E1 by using 3-(isoindolin-2-yl)propane-1-amine dihydrochloride 1.4c (0.57 mmol, 140 mg), and 4-chlorobenzoylchloride (0.57 mmol, 100 mg). Purification by column chromatography (DCM:MeOH(NH$_3$), 9:1 (v/v)) was performed. Yield: 36%. $^1$H NMR (300 MHz, CDCl$_3$), δ: 9.00 (br s, 1H, NH); 7.48 (d, J=8.6 Hz, 2H, H$_2$, H$_6$); 7.31-7.21 (m, 4H, H$_{aro}$); 7.03 (d, J=8.5 Hz, 2H, H$_3$, H$_5$); 4.02 (s, 4H, 2CH$_2$); 3.63 (q, J=5.0 Hz, 2H, CH$_2$); 3.05 (t, J=5.8 Hz, 2H, CH$_2$); 1.89 (p, J=5.8 Hz, 2H, CH$_2$). $^{13}$C NMR (75 MHz, CDCl$_3$) δ: 165.6 (CO); 139.2 (2 C$_{aro}$); 137.1 (C$_{aro}$); 132.6 (C$_{aro}$); 128.4 (2 C$_{aro}$); 128.2 (2 C$_{aro}$); 127.2 (2 C$_{aro}$); 122.4 (2 C$_{aro}$); 58.6 (2 CH$_2$); 55.3 (CH$_2$); 40.8 (CH$_2$); 25.9 (CH$_2$). LCMS m/z 315.0, 317.0 [M+H]$^+$.

Example 13: Synthesis of N-[3-(benzylmethylamino)propyl]-2-bromobenzamide (Compound 3.1.20)

The compound 3.1.20 was synthesized according to the procedure E1 by using N$^1$-benzyl-N$^1$-methylpropane-1,3- diamine dihydrochloride 1.4a (0.45 mmol, 113 mg), and 2-bromobenzoylchloride (0.45 mmol, 100 mg). Purification by column chromatography (DCM:MeOH(NH$_3$), 9:1 (v/v)) was performed. Yield: 52%. $^1$H NMR (300 MHz, CDCl$_3$), δ: 7.56 (dd, J=7.8 Hz, J=1.3 Hz, 1H, H$_6$); 7.47 (br s, 1H, NH); 7.37 (dd, J=7.4 Hz, J=2.0 Hz, 1H, H$_3$); 7.31 (td, J=7.3 Hz, J=1.2 Hz, 1H, H$_{aro}$); 7.24 (td, J=7.4 Hz, J=1.9 Hz, 1H, H$_{aro}$); 7.16-7.07 (m, 5H, H$_{aro}$); 3.52 (q, J=6.2 Hz, 2H, CH$_2$); 3.48 (s, 2H, CH$_2$); 2.57 (t, J=6.1 Hz, 2H, CH$_2$); 2.19 (s, 3H, NCH$_3$); 1.80 (p, J=6.2 Hz, 2H, CH$_2$). $^{13}$C NMR (75 MHz, CDCl$_3$) δ: 167.8 (CO); 138.6 (C$_{aro}$); 138.0 (C$_{aro}$); 133.2 (C$_{aro}$); 130.8 (C$_{aro}$); 129.0 (2 C$_{aro}$); 128.9 (2 C$_{aro}$); 128.3 (C$_{aro}$); 127.4 (C$_{aro}$); 127.1 (C$_{aro}$); 119.5 (C$_{aro}$); 62.6 (CH$_2$); 56.1 (CH$_2$); 41.8 (CH$_3$); 39.6 (CH$_2$); 25.3 (CH$_2$). LCMS m/z 361.0, 363.0 [M+H]$^+$.

Example 14: Synthesis of N-[3-(benzylmethyl-amino)propyl]-3-bromobenzamide (Compound 3.1.21)

The compound 3.1.21 was synthesized according to the procedure E1 by using N$^1$-benzyl-N$^1$-methylpropane-1,3-diamine dihydrochloride 1.4a (0.45 mmol, 113 mg), and 3-bromobenzoylchloride (0.45 mmol, 100 mg). Purification by column chromatography (DCM:MeOH(NH$_3$), 9:1 (v/v)) was performed. Yield: 53%. $^1$H NMR (300 MHz, CDCl$_3$), δ: 8.27 (br s, 1H, NH); 7.82 (t, J=1.8 Hz, 2H, H$_2$); 7.55 (m, 1H, H$_5$); 7.28-7.17 (m, 7H, H$_4$, H$_6$, H$_{aro}$); 3.55 (m, 4H, 2CH$_2$); 2.62 (t, J=6.0 Hz, 2H, CH$_2$); 2.30 (s, 3H, NCH$_3$); 1.83 (p, J=5.9 Hz, 2H, CH$_2$). $^{13}$C NMR (75 MHz, CDCl$_3$) δ: 165.7 (CO); 137.6 (C$_{aro}$); 136.7 (C$_{aro}$); 134.0 (C$_{aro}$); 130.3 (C$_{aro}$); 129.9 (C$_{aro}$); 129.4 (2 C$_{aro}$); 128.5 (2 C$_{aro}$); 127.6 (C$_{aro}$); 125.4 (C$_{aro}$); 122.6 (C$_{aro}$); 63.1 (CH$_2$); 56.8 (CH$_2$); 41.8 (CH$_3$); 40.4 (CH$_2$); 24.9 (CH$_2$). LCMS m/z 361.0, 363.0 [M+H]$^+$.

Example 15: Synthesis of N-[3-(benzylmethyl-amino)propyl]-4-bromobenzamide (Compound 3.1.22)

The compound 3.1.22 was synthesized according to the procedure E2 by using N$^1$-benzyl-N$^1$-methylpropane-1,3-diamine dihydrochloride 1.4a (0.65 mmol, 164 mg), and 4-fluorobenzoic acid (0.65 mmol, 130 mg). Purification by thick layer chromatography (DCM:MeOH(NH$_3$), 9:1 (v/v)) was performed. Yield: 67%. $^1$H NMR (300 MHz, CDCl$_3$), δ: 8.29 (br s, 1H, NH); 7.54 (d, J=9.1 Hz, 2H, H$_2$, H$_6$); 7.46 (d, J=9.2 Hz, 2H, H$_3$, H$_5$); 7.33-7.20 (m, 5H, H$_{aro}$); 3.65-3.47 (m, 4H, 2 CH$_2$); 2.66 (t, J=5.9 Hz, 2H, CH$_2$); 2.29 (s, 3H, CH$_3$); 1.84 (p, J=5.8 Hz, 2H, CH$_2$). $^{13}$C NMR (75 MHz, CDCl$_3$) δ: 166.2 (CO); 137.5 (C$_{aro}$); 133.5 (C$_{aro}$); 131.6 (2 C$_{aro}$); 129.5 (2 C$_{aro}$); 128.6 (2 C$_{aro}$); 128.5 (2 C$_{aro}$); 127.7 (C$_{aro}$); 125.7 (C$_{aro}$); 63.0 (CH$_2$); 57.0 (CH$_2$); 41.4 (CH$_3$); 40.3 (CH$_2$); 24.9 (CH$_2$). LCMS m/z 360.9, 362.9 [M+H]$^+$.

Example 16: Synthesis of N-[3-(benzylmethyl-amino)propyl]-2,3-dichlorobenzamide (Compound 3.1.23)

The compound 3.1.23 was synthesized according to the procedure E1 by using N$^1$-benzyl-N$^1$-methylpropane-1,3-diamine dihydrochloride 1.4a (0.48 mmol, 120 mg), and 2,3-dichlorobenzoylchloride (0.48 mmol, 100 mg). Purification by column chromatography (DCM:MeOH(NH$_3$), 9:1 (v/v)) was performed. Yield: 66%. $^1$H NMR (300 MHz, CDCl$_3$) δ: 7.58 (br s, 1H, NH); 7.51 (dd, J=7.9 Hz, J=1.6 Hz, 1H, H$_6$); 7.32 (dd, J=7.7 Hz, J=1.6 Hz, 1H, H$_4$); 7.25 (m, 1H, H$_5$); 7.17-7.07 (m, 5H, H$_{aro}$); 3.55 (q, J=6.7 Hz, 2H, CH$_2$); 3.48 (s, 2H, CH$_2$); 2.58 (t, J=5.9 Hz, 2H, CH$_2$); 2.21 (s, 3H, NCH$_3$); 1.82 (p, J=6.0 Hz, 2H, CH$_2$). $^{13}$C NMR (75 MHz, CDCl$_3$) δ: 166.2 (CO); 138.6 (C$_{aro}$); 137.8 (C$_{aro}$); 133.7 (C$_{aro}$); 131.3 (C$_{aro}$); 128.9 (C$_{aro}$); 128.3 (2 C$_{aro}$); 127.6 (2 C$_{aro}$); 127.5 (C$_{aro}$); 127.3 (C$_{aro}$); 127.0 (C$_{aro}$); 62.7 (CH$_2$); 56.0 (CH$_2$); 41.8 (CH$_3$); 39.7 (CH$_2$); 25.1 (CH$_2$). LCMS m/z 351.0, 353.0 [M+H]$^+$.

Example 17: Synthesis of N-[3-(benzylmethyl-amino)propyl]-2,4-dichlorobenzamide (Compound 3.1.24)

The compound 3.1.24 was synthesized according to the procedure E1 by using N$^1$-benzyl-N$^1$-methylpropane-1,3-diamine dihydrochloride 1.4a (0.48 mmol, 120 mg), and 2,4-dichlorobenzoylchloride (0.48 mmol, 100 mg). Purification by column chromatography (DCM:MeOH(NH$_3$), 9:1 (v/v)) was performed. Yield: 41%. $^1$H NMR (300 MHz, CDCl$_3$), δ: 7.70 (br s, 1H, NH); 7.45 (d, J=8.3 Hz, 1H, H$_6$); 7.38 (d, J=2.0 Hz, 1H, H$_3$); 7.26 (dd, J=8.3 Hz, J=2.0 Hz 1H, H$_5$); 7.19-7.07 (m, 5H, H$_{aro}$); 3.53 (q, J=5.6 Hz, 2H, CH$_2$); 3.47 (s, 2H, CH$_2$); 2.56 (t, J=6.2 Hz, 2H, CH$_2$); 2.20 (s, 3H, NCH$_3$); 1.81 (p, J=6.0 Hz, 2H, CH$_2$). $^{13}$C NMR (75 MHz, CDCl$_3$) δ: 165.7 (CO); 137.9 (C$_{aro}$); 136.1 (C$_{aro}$); 134.5 (C$_{aro}$); 131.6 (C$_{aro}$); 130.5 (C$_{aro}$); 129.9 (C$_{aro}$); 128.9 (2 C$_{aro}$); 128.3 (2 C$_{aro}$); 127.3 (C$_{aro}$); 127.2 (C$_{aro}$); 62.6 (CH$_2$); 56.2 (CH$_2$); 41.8 (CH$_3$); 39.9 (CH$_2$); 25.1 (CH$_2$). LCMS m/z 351.0, 353.0 [M+H]$^+$.

Example 18: Synthesis of N-[3-(benzylmethyl-amino)propyl]-3,4-dichlorobenzamide (Compound 3.1.25)

The compound 3.1.25 was synthesized according to the procedure E2 by using N$^1$-benzyl-N$^1$-methylpropane-1,3-diamine dihydrochloride 1.4a (0.78 mmol, 197 mg), and 3,4-dichlorobenzoic acid (0.78 mmol, 150 mg). Purification by thick layer chromatography (DCM:MeOH(NH$_3$), 9:1 (v/v)) was performed. Yield: 31%. $^1$H NMR (300 MHz, CDCl$_3$), δ: 8.44 (br s, 1H, NH); 7.82 (d, 0.1=2.0 Hz, 1H, H$_2$); 7.47 (dd, J=8.2 Hz, J=2.0 Hz, 1H, H$_6$); 7.38 (d, J=8.3 Hz, 1H, H$_5$); 7.31-7.22 (m, 5H, H$_{aro}$); 3.60 (s, 2H, CH$_2$); 3.56 (q, J=6.1 Hz, 2H, CH$_2$); 2.68 (t, J=6.1 Hz, 2H, CH$_2$); 2.33 (s, 3H, CH$_3$); 1.86 (p, J=6.2 Hz, 2H, CH$_2$). $^{13}$C NMR (75 MHz, CDCl$_3$) δ: 164.9 (CO); 135.4 (C$_{aro}$); 134.5 (C$_{aro}$); 132.9 (C$_{aro}$); 130.4 (2 C$_{aro}$); 129.5 (2 C$_{aro}$); 129.3 (C$_{aro}$); 128.6 (2 C$_{aro}$); 127.8 (C$_{aro}$); 126.1 (C$_{aro}$); 62.8 (CH$_2$); 56.7 (CH$_2$); 41.4 (CH$_3$); 40.3 (CH$_2$); 24.7 (CH$_2$). LCMS m/z 350.9, 352.9 [M+H]$^+$.

Example 19: Synthesis of N-[3-(benzylmethyl-amino)propyl]-3,5-dichlorobenzamide (Compound 3.1.26)

The compound 3.1.26 was synthesized according to the procedure E2 by using N$^1$-benzyl-N$^1$-methylpropane-1,3-diamine dihydrochloride 1.4a (0.78 mmol, 197 mg), and 3,5-dichlorobenzoic acid (0.78 mmol, 150 mg). Purification by thick layer chromatography (DCM:MeOH(NH$_3$), 9:1 (v/v)) was performed. Yield: 34%. $^1$H NMR (300 MHz, CDCl$_3$), δ: 8.42 (br s, 1H, NH); 7.55 (m, 2H, H$_2$, H$_6$); 7.44 (m, 1H, H$_4$); 7.28-7.20 (m, 5H, H$_{aro}$); 3.57-3.51 (m, 4H, 2 CH$_2$); 2.63 (t, J=6.1 Hz, 2H, CH$_2$); 2.32 (s, 3H, CH$_3$); 1.82 (p, J=6.0 Hz, 2H, CH$_2$). $^{13}$C NMR (75 MHz, CDCl$_3$) δ: 164.6 (CO); 137.7 (C$_{aro}$); 137.5 (C$_{aro}$); 135.3 (C$_{aro}$); 130.9 (2 C$_{aro}$); 129.3 (2 C$_{aro}$); 128.5 (2 C$_{aro}$); 127.6 (C$_{aro}$); 125.7

(2 $C_{aro}$); 63.0 ($CH_2$); 56.7 ($CH_2$); 41.8 ($CH_3$); 40.7 ($CH_2$); 24.8 ($CH_2$). LCMS m/z 351.0, 353.0 $[M+H]^+$.

Example 20: Synthesis of N-[3-(benzylmethylamino)propyl]-4-bromo-2-fluorobenzamide (Compound 3.1.27)

The compound 3.1.27 was synthesized according to the procedure E1 by using $N^1$-benzyl-$N^1$-methylpropane-1,3-diamine dihydrochloride 1.4a (0.42 mmol, 105 mg), and 4-bromo-2-fluorobenzoylchloride (0.42 mmol, 100 mg). Purification by column chromatography (DCM:MeOH (NH$_3$), 9:1 (v/v)) was performed. Yield: 22%. $^1$H NMR (300 MHz, MeOD), δ: 7.60 (d, J=8.2 Hz, 1H, H$_6$); 7.50 (m, 1H, H$_{aro}$); 7.44 (m, 1H, H$_{aro}$); 7.22-7.34 (m, 5H, H$_{aro}$); 3.59 (s, 2H, CH$_2$); 3.43 (t, J=6.7 Hz, 2H, CH$_2$); 2.56 (t, J=7.1 Hz, 2H, CH$_2$); 2.28 (s, 3H, CH$_3$); 1.85 (p, J=7.0 Hz, 2H, CH$_2$). $^{13}$C NMR (75 MHz, CDCl$_3$) δ: 162.5 (CO); 132.9 ($C_{aro}$); 129.5 ($C_{aro}$); 128.7 ($C_{aro}$); 128.4 (2 $C_{aro}$); 128.1 (2 $C_{aro}$); 125.1 ($C_{aro}$); 119.8 ($C_{aro}$); 119.4 ($C_{aro}$); 62.4 (CH$_2$); 55.3 (CH$_2$); 41.4 (CH$_3$); 29.7 (CH$_2$); 25.4 (CH$_2$). LCMS m/z 379.0, 381.0 $[M+H]^+$.

Example 21: Synthesis of N-[3-(benzylmethylamino)propyl]-3-methoxybenzamide (Compound 3.1.28)

The compound 3.1.28 was synthesized according to the procedure E1 by using $N^1$-benzyl-$N^1$-methylpropane-1,3-diamine dihydrochloride 1.4a (0.59 mmol, 148 mg), and 3-methoxybenzoylchloride (0.59 mmol, 100 mg). Purification by column chromatography (DCM:MeOH(NH$_3$), 9:1 (v/v)) was performed. Yield: 35%. $^1$H NMR (300 MHz, CDCl$_3$), δ: 8.10 (br s, 1H, NH); 7.35 (m, 1H, H$_2$); 7.28-7.14 (m, 7H, H$_5$, H$_6$, H$_{aro}$); 7.11 (m, 1H, H$_4$); 3.78 (s, 3H, OCH$_3$); 3.55 (m, 4H, 2CH$_2$); 2.63 (t, J=6.2 Hz, 2H, CH$_2$); 2.28 (s, 3H, NCH$_3$); 1.83 (p, J=6.4 Hz, 2H, CH$_2$). $^{13}$C NMR (75 MHz, CDCl$_3$) δ: 165.3 (CO); 159.7 ($C_{aro}$); 137.6 ($C_{aro}$); 136.2 ($C_{aro}$); 129.4 (3 $C_{aro}$); 128.4 (2 $C_{aro}$); 127.4 ($C_{aro}$); 118.8 ($C_{aro}$); 117.6 ($C_{aro}$); 112.1 ($C_{aro}$); 63.0 (CH$_2$); 56.8 (CH$_2$); 55.3 (OCH$_3$); 41.5 (NCH$_3$); 40.2 (CH$_2$); 25.2 (CH$_2$). LCMS m/z 313.0 $[M+H]^+$.

Example 22: Synthesis of N-[3-(benzylmethylamino)propyl]-4-methoxybenzamide (Compound 3.1.29)

The compound 3.1.29 was synthesized according to the procedure E2 by using $N^1$-benzyl-$N^1$-methylpropane-1,3-diamine dihydrochloride 1.4a (0.98 mmol, 247 mg), and 4-methoxybenzoic acid (0.98 mmol, 150 mg). Purification by thick layer chromatography (DCM:MeOH(NH$_3$), 9:1 (v/v)) was performed. Yield: 73%. $^1$H NMR (300 MHz, CDCl$_3$), δ: 7.97 (br s, 1H, NH); 7.67 (m, 2H, H$_2$, H$_6$); 7.32-7.24 (m, 5H, H$_{aro}$); 6.84 (m, 2H, H$_3$, H$_5$); 3.84 (s, 3H, OCH$_3$); 3.60-3.52 (m, 4H, 2 CH$_2$); 2.65 (t, J=6.0 Hz, 2H, CH$_2$); 2.29 (s, 3H, CH$_3$); 1.85 (p, J=6.1 Hz, 2H, CH$_2$). $^{13}$C NMR (75 MHz, CDCl$_3$) δ: 166.9 (CO); 162.0 ($C_{aro}$); 137.2 ($C_{aro}$); 129.6 (2 $C_{aro}$); 128.8 (2 $C_{aro}$); 128.5 (2 $C_{aro}$); 127.7 ($C_{aro}$); 125.0 ($C_{aro}$); 113.6 (2 $C_{aro}$); 62.9 (CH$_2$); 56.7 (CH$_2$); 55.4 (OCH$_3$); 41.4 (CH$_3$); 39.9 (CH$_2$); 25.3 (CH$_2$). LCMS m/z 313.1 $[M+H]^+$.

Example 23: Synthesis of N-[3-(benzylmethylamino)propyl]-3-dimethylaminobenzamide (Compound 3.1.30)

The compound 3.1.30 was synthesized according to the procedure E1 by using $N^1$-benzyl-$N^1$-methylpropane-1,3-diamine dihydrochloride 1.4a (0.55 mmol, 138 mg), and 3-dimethylaminobenzoylchloride (0.55 mmol, 100 mg). Purification by column chromatography (DCM:MeOH (NH$_3$), 9:1 (v/v)) was performed. Yield: 11%. $^1$H NMR (300 MHz, CDCl$_3$), δ: 7.90 (br s, 1H, NH); 7.28-7.24 (m, 5H, H$_{aro}$); 7.22-7.19 (m, 2H, H$_2$, H$_5$); 6.92 (d, J=7.5 Hz, 1H, H$_6$); 6.82 (dd, J=8.1 Hz, J=2.2 Hz, 1H, H$_4$); 3.62-3.51 (m, 4H, 2 CH$_2$); 2.95 (s, 6H, 2 CH$_3$); 2.64 (t, J=6.0 Hz, 2H, CH$_2$); 2.31 (s, 3H, CH$_3$); 1.85 (p, J=5.8 Hz, 2H, CH$_2$). $^{13}$C NMR (75 MHz, CDCl$_3$) δ: 162.4 (CO); 138.5 ($C_{aro}$); 133.1 (2 $C_{aro}$); 129.0 (2 $C_{aro}$); 128.2 (2 $C_{aro}$); 128.0 (2 $C_{aro}$); 127.1 ($C_{aro}$); 119.7 ($C_{aro}$); 119.4 ($C_{aro}$); 63.0 (CH$_2$); 55.9 (CH$_2$); 50.9 (CH$_2$); 41.9 (3 CH$_3$); 39.9 (CH$_2$); 25.6 (CH$_2$). LCMS m/z 326.0 $[M+H]^+$.

Example 24: Synthesis of N-[3-(benzylmethylamino)propyl]-4-cyanobenzamide (Compound 3.1.31)

The compound 3.1.31 was synthesized according to the procedure E1 by using $N^1$-benzyl-$N^1$-methylpropane-1,3-diamine dihydrochloride 1.4a (0.60 mmol, 150 mg), and 4-cyanobenzoylchloride (0.60 mmol, 100 mg). Purification by column chromatography (DCM:MeOH(NH$_3$), 9:1 (v/v)) was performed. Yield: 7%. $^1$H NMR (300 MHz, CDCl$_3$), δ: 8.61 (br s, 1H, NH); 7.71 (d, J=8.2 Hz, 2H, H$_2$, H$_6$); 7.61 (d, J=8.3 Hz, 2H, H$_3$, H$_5$); 7.30-7.20 (m, 5H, H$_{aro}$); 3.62 (q, J=6.4 Hz, 2H, CH$_2$); 3.55 (s, 2H, CH$_2$); 2.69 (t, J=5.8 Hz, 2H, CH$_2$); 2.27 (s, 3H, CH$_3$); 1.84 (p, J=6.0 Hz, 2H, CH$_2$). $^{13}$C NMR (75 MHz, CDCl$_3$) δ: 165.3 (CO); 138.4 ($C_{aro}$); 136.8 ($C_{aro}$); 132.2 (2 $C_{aro}$); 129.6 (2 $C_{aro}$); 128.6 (2 $C_{aro}$); 127.7 (2 $C_{aro}$); 118.2 ($C_{aro}$); 114.6 ($C_{aro}$); 63.3 (CH$_2$); 57.6 (CH$_2$); 41.5 (CH$_3$); 40.9 (CH$_2$); 25.1 (CH$_2$). LCMS m/z 308.0 $[M+H]^+$.

Example 25: Synthesis of N-[3-(benzylmethylamino)propyl]-4-nitrobenzamide (Compound 3.1.32)

The compound 3.1.32 was synthesized according to the procedure E1 by using $N^1$-benzyl-$N^1$-methylpropane-1,3-diamine dihydrochloride 1.4a (0.53 mmol, 133 mg), and 4-nitrobenzoylchloride (0.53 mmol, 100 mg). Purification by column chromatography (DCM:MeOH(NH$_3$), 9:1 (v/v)) was performed. Yield: 50%. $^1$H NMR (300 MHz, CDCl$_3$), δ: 8.68 (br s, 1H, NH); 8.17 (d, J=8.8 Hz, 2H, H$_2$, H$_6$); 7.79 (d, J=8.8 Hz, 2H, H$_3$, H$_5$); 7.32-7.22 (m, 5H, H$_{aro}$); 3.65-3.56 (m, 4H, 2CH$_2$); 2.72 (t, J=5.6 Hz, 2H, CH$_2$); 2.32 (s, 3H, NCH$_3$); 1.88 (p, J=5.7 Hz, 2H, CH$_2$). $^{13}$C NMR (75 MHz, CDCl$_3$) δ: 166.7 (CO); 149.3 ($C_{aro}$); 140.1 ($C_{aro}$); 137.1 ($C_{aro}$); 129.6 (2 $C_{aro}$); 128.6 (2 $C_{aro}$); 128.1 (2 $C_{aro}$); 127.8 ($C_{aro}$); 123.6 (2 $C_{aro}$); 63.5 (CH$_2$); 57.6 (CH$_2$); 41.7 (CH$_3$); 41.1 (CH$_2$); 25.0 (CH$_2$). LCMS m/z 328.0 $[M+H]^+$.

Example 26: Synthesis of N-[3-(benzylmethylamino)propyl]-4-chlorobenzensulfonamide (Compound 3.2a)

The compound 3.2a was synthesized according to the procedure E1 by using of $N^1$-benzyl-$N^1$-methylpropane-1,3-diamine dihydrochloride 1.4a (0.47 mmol, 118 mg), and 4-chlorobenzo sulfonamide chloride (0.47 mmol, 100 mg). Purification by column chromatography (petroleum ether: DCM:MeOH(NH$_3$), 5:4:1 (v/v)) was performed. Yield: 60%. $^1$H NMR (300 MHz, CDCl$_3$), δ: 7.76 (d, J=9.1 Hz, 2H, H$_2$, H$_6$); 7.47 (d, J=9.2 Hz, 2H, H$_3$, H$_5$); 7.36-7.22 (m, 5H, H$_{aro}$); 3.46 (s, 2H, CH$_2$); 3.05 (t, J=7.2 Hz, 2H, CH$_2$); 2.45

(t, J=7.1 Hz, 2H, CH$_2$); 2.18 (s, 3H, CH$_3$); 1.67 (p, J=7.0 Hz, 2H, CH$_2$). $^{13}$C NMR (75 MHz, CDCl$_3$) δ: 138.8 (C$_{aro}$); 138.7 (C$_{aro}$); 137.9 (C$_{aro}$); 129.3 (2 C$_{aro}$); 129.0 (2 C$_{aro}$); 128.6 (2 C$_{aro}$); 128.5 (2 C$_{aro}$); 127.4 (C$_{aro}$); 62.8 (CH$_2$); 56.8 (CH$_2$); 44.0 (CH$_3$); 41.9 (CH$_2$); 24.7 (CH$_2$). LCMS m/z 353.0, 355.0 [M+H]$^+$.

Example 27: Synthesis of 4-(benzylmethylamino)-N-(4-chlorophenyl)butanamide (Compound 3.3a)

The compound 3.3a was synthesized according to the procedure E3 by using of 4-chloro-N-(4-chlorophenyl)butyramide 2.2 (1.29 mmol, 300 mg) and N-benzylmethylamine (7.75 mmol, 1 mL). Purification by thick layer chromatography (cyclohexane:ethyl acetate:MeOH(NH$_3$), 4.5:4.5:1 (v/v)) was performed. Yield: 70%. $^1$H NMR (300 MHz, CDCl$_3$), 9.63 (br s, 1H, NH); 7.45 (d, J=9.1 Hz, 2H, H$_2$, H$_6$); 7.34-7.27 (m, 5H, H$_{aro}$); 7.21 (d, J=9.0 Hz, 2H, H$_3$, H$_5$); 3.69 (s, 2H, CH$_2$); 2.62 (t, J=6.2 Hz, 2H, CH$_2$); 2.51 (t, J=7.0 Hz, 2H, CH$_2$); 2.35 (s, 3H, CH$_3$); 1.96 (p, J=6.1 Hz, 2H, CH$_2$). $^{13}$C NMR (75 MHz, CDCl$_3$) δ: 171.4 (CO); 137.2 (C$_{aro}$); 135.9 (C$_{aro}$); 129.7 (2 C$_{aro}$); 128.8 (2 C$_{aro}$); 128.7 (2 C$_{aro}$); 128.5 (2 C$_{aro}$); 128.0 (C$_{aro}$); 120.8 (C$_{aro}$); 62.2 (CH$_2$); 56.5 (CH$_2$); 41.4 (CH$_3$); 36.2 (CH$_2$); 22.2 (CH$_2$). LCMS m/z 317.2, 319.2 [M+H]$^+$.

Example 28: Synthesis of N-(4-chlorobenzyl)-3-(benzylmethylamino)propanamide (Compound 3.4a)

The compound 3.4a was synthesized according to the procedure E3 by using of N-(4-chlorobenzyl)-3-chloropanamide 2.3 (0.21 mmol, 50 mg) and N-benzylmethylamine (1.29 mmol, 166 μL). Purification by thick layer chromatography (cyclohexane:ethyl acetate:MeOH(NH$_3$), 4.5:4.5:1 (v/v)). Yield: 67%. $^1$H NMR (300 MHz, CDCl$_3$), δ: 8.65 (br s, 1H, NH); 7.34-7.19 (m, 7H, H$_2$, H$_6$, H$_{aro}$); 7.09 (d, J=9.3 Hz, 2H, H$_3$, H$_5$); 4.38 (d, J=6.1 Hz, 2H, CH$_2$); 3.57 (s, 2H, CH$_2$); 2.79 (t, J=6.2 Hz, 2H, CH$_2$); 2.56 (t, J=6.0 Hz, 2H, CH$_2$); 2.25 (s, 3H, CH$_3$). $^{13}$C NMR (75 MHz, CDCl$_3$) δ: 171.9 (CO); 137.2 (C$_{aro}$); 133.1 (C$_{aro}$); 129.3 (2 C$_{aro}$); 129.2 (3 C$_{aro}$); 128.8 (2 C$_{aro}$); 128.6 (2 C$_{aro}$); 127.9 (C$_{aro}$); 62.0 (CH$_2$); 53.0 (CH$_2$); 42.6 (CH$_2$); 40.7 (CH$_3$); 32.4 (CH$_2$). LCMS m/z 316.9, 318.9 [M+H]$^+$.

Example 29: Synthesis of N-(4-chlorobenzyl)-3-(benzylmethylamino)propanamine (Compound 3.5a)

The compound 3.5a was synthesized according to the procedure E4 by using commercially 4-chlorobenzaldehyde (0.55 mmol, 77 mg) and N$^1$-benzyl-N$^1$-methylpropane-1,3-diamine 1.4a (0.55 mmol, 100 mg). Purification by thick layer chromatography (DCM:MeOH(NH$_3$), 9:1 (v/v)). Yield: 35%. $^1$H NMR (300 MHz, CDCl$_3$), δ: 7.80 (br s, 1H, NH); 7.48 (d, J=8.4 Hz, 2H, H$_2$, H$_6$); 7.33 (d, J=8.5 Hz, 2H, H$_3$, H$_5$); 7.30-7.26 (m, 3H, H$_{aro}$); 7.13 (m, 2H, H$_{aro}$); 4.00 (s, 2H, CH$_2$); 3.53 (s, 2H, CH$_2$); 2.94 (t, J=6.5 Hz, 2H, CH$_2$); 2.60 (t, J=6.3 Hz, 2H, CH$_2$); 2.27 (s, 3H, CH$_3$); 2.02 (p, J=6.2 Hz, 2H, CH$_2$). $^{13}$C NMR (75 MHz, CDCl$_3$) δ: 136.5 (C$_{aro}$); 135.3 (C$_{aro}$); 131.2 (2 C$_{aro}$); 130.3 (C$_{aro}$); 129.4 (2 C$_{aro}$); 129.3 (2 C$_{aro}$); 128.6 (2 C$_{aro}$); 127.8 (C$_{aro}$); 62.2 (CH$_2$); 55.4 (CH$_2$); 50.9 (CH$_2$); 47.3 (CH$_2$); 41.5 (CH$_3$); 22.6 (CH$_2$). LCMS m/z 303.0, 305.0 [M+H]$^+$.

Example 30 Synthesis of N-(2-(benzyl(methyl)amino)ethyl)-3-chlorobenzamide (Compound 3.1.33)

The compound 3.1.33 was synthesized according to the procedure E3 by using N-(2-aminoethyl)benzamide (0.91 mmol, 150 mg) and 3-chlorobenzoyl chloride (0.91 mmol, 117 μL). Purification by thick layer chromatography (DCM:MeOH(NH$_3$), 9.1:1 (v/v)). Yield 35%. $^1$H NMR (300 MHz, CDCl$_3$) δ: 2.26 (s, 3H), 2.56 (t, 2H, J=7.1 Hz), 3.56 (q, 2H, J=5.0 Hz, J=7.5 Hz), 3.60 (s, 2H), 6.85 (s, 1H), 7.31 (m, 5H), 7.35 (t, 1H, J=7.5 Hz, J=7.5 Hz), 7.74 (m, 1H), 7.56 (d, 1H, J=1.5 Hz), 7.93 (m, 2H) $^{13}$C NMR (75 MHz, CDCl$_3$) δ: 44.1, 57.6, 57.9, 64.9, 127.1, 127.8, 128.6, 128.2, 129.7, 130.0, 132.2, 134.4, 135.6, 138.6, 167.3 LCMS m/z 302.1; 303.1 [M+H]$^+$.

Example 31: Synthesis of N-(2-(benzyl(methyl)amino)ethyl)-2,4-dichlorobenzamide (Compound 3.1.34)

The compound 3.1.34 was synthesized according to the procedure E3 by using N-(2-aminoethyl)benzamide (0.91 mmol, 150 mg) and 2,4-dichlorobenzoyl chloride (0.91 mmol, 107 μL). Purification by thick layer chromatography (DCM:MeOH(NH$_3$), 9.1:1 (v/v)). Yield 35%. $^1$H NMR (300 MHz, CDCl$_3$) δ: 2.26 (s, 3H), 2.56 (t, 2H, J=7.1 Hz), 3.56 (q, 2H, J=5.0 Hz, J=7.5 Hz), 3.60 (s, 2H), 6.85 (s, 1H), 7.31 (m, 5H), 7.35 (t, 1H, J=7.5 Hz, J=7.5 Hz), 7.74 (m, 1H), 7.56 (d, 1H, J=1.5 Hz), 7.93 (m, 2H) $^{13}$C NMR (75 MHz, CDCl$_3$) δ: 44.1, 57.6, 57.9, 64.9, 127.1, 127.8, 128.6, 128.2, 129.7, 130.0, 132.2, 134.4, 135.6, 138.6, 167.3 LCMS m/z 302.1; 303.1 [M+H]$^+$.

Example 32: Synthesis of N-(2-(benzyl(methyl)amino)ethyl)-4-cyanobenzamide (Compound 3.1.36)

The compound 3.1.36 was synthesized according to the procedure E3 by using N-(2-aminoethyl)benzamide (0.91 mmol, 150 mg) and 4-cyanobenzolyl chloride (0.91 mmol, 150 mg). Purification by thick layer chromatography (DCM:MeOH(NH$_3$), 9.1:1 (v/v)). Yield 33%. $^1$H NMR (300 MHz, CDCl$_3$) δ: 2.34 (s, 3H), 2.65 (t, 2H, J=5.7 Hz), 3.55 (q, 2H, J=5.1 Hz, J=6.3 Hz), 3.59 (s, 2H), 6.96 (s, 1H), 7.35 (m, 5H), 7.52 (d, 2H, J=4.8 Hz), 8.29 (d, 2H, J=9 Hz) $^{13}$C NMR (75 MHz, CDCl$_3$) δ: 43.9, 57.5, 58.0, 64.7, 115.7, 118.0, 126.9, 128.0, 128.5, 131.7, 139.1, 167.9 LCMS m/z 294.1 [M+H]$^+$.

Example 33: Synthesis of N-(2-(benzyl(methyl)amino)ethyl)-4-nitrobenzamide (Compound 3.1.37)

The compound 3.1.37 was synthesized according to the procedure E3 by using N-(2-aminoethyl)benzamide (0.91 mmol, 150 mg) and 4-nitrobenzoyl chloride (0.91 mmol, 110 mg). Purification by thick layer chromatography (DCM:MeOH(NH$_3$), 9.1:1 (v/v)). Yield 52%. $^1$H NMR (300 MHz, CDCl$_3$) δ: 2.34 (s, 3H), 2.65 (t, 2H, J=5.7 Hz), 3.55 (q, 2H, J=5.1 Hz, J=6.3 Hz), 3.59 (s, 2H), 6.96 (s, 1H), 7.35 (m, 5H), 7.52 (d, 2H, J=4.8 Hz), 8.29 (d, 2H, J=9 Hz) $^{13}$C NMR (75 MHz, CDCl$_3$) δ: 43.9, 57.5, 58.0, 64.7, 115.7, 118.0, 126.9, 128.0, 128.5, 131.7, 139.1, 167.9 LCMS m/z 294.1 [M+H]$^+$.

Example 34: Synthesis of N-(4-Nitrobenzyl)-3-(benzylmethylamino)propanamide (Compound 3.4b)

The compound 3.4b was synthesized according to the procedure E3 by using N-(4-chlorobenzyl)-3-chloropanamide 2.3b (0.41 mmol, 100 mg) and N-benzylmethylamine (4.1 mmol, 531 μL). Purification by thick layer chromatography (DCM:MeOH(NH$_3$), 9.7:0.3 (v/v)). Yield: 37%. $^1$H NMR (300 MHz, CDCl$_3$), δ: 9.00 (br s, 1H, NH); 8.15 (d, J=8.7 Hz, 2H, H$_{aro}$); 7.40 (d, J=8.4 Hz, 2H, H$_{aro}$);

7.20 (m, 3H, H$_{aro}$); 7.10 (m, 2H, H$_{aro}$); 4.50 (d, J=6.0 Hz, 2H, CH$_2$); 3.50 (s, 2H, CH$_2$); 2.70 (t, J=6.2 Hz, 2H, CH$_2$); 2.50 (t, J=6.2 Hz, 2H, CH$_2$); 2.25 (s, 3H, CH$_3$). $^{13}$C NMR (75 MHz, CDCl$_3$) δ: 172.6 (CO); 146.5 (C$_{aro}$); 146.2 (C$_{aro}$); 137.3 (C$_{aro}$); 129.1 (C$_{aro}$); 128.5 (C$_{aro}$); 128.1 (C$_{aro}$); 127.6 (C$_{aro}$); 123.8 (C$_{aro}$); 62.2 (CH$_2$); 52.8 (CH$_2$); 42.3 (CH$_3$); 41.1 (CH$_2$); 32.5 (CH$_2$); 29.7 (CH$_2$). LCMS m/z 328.9 [M+H]$^+$.

Example 35: Synthesis of N-(4-Cyanobenzyl)-3-(benzylmethylamino)propanamide (Compound 3.4c)

The compound 3.4c was synthesized according to the procedure E3 by using N-(4-chlorobenzyl)-3-chloropropanamide 2.3c (0.44 mmol, 100 mg) and N-benzylmethylamine (4.4 mmol, 579 µL). Purification by thick layer chromatography (DCM:MeOH(NH$_3$), 9.7:0.3 (v/v)). Yield: 80%. $^1$H NMR (300 MHz, CDCl$_3$), δ: 8.90 (br s, 1H, NH); 7.58 (d, J=6.3 Hz, 2H, H$_{aro}$); 7.32 (d, J=8.1 Hz, 2H, H$_{aro}$); 7.21 (m, 3H, H$_{aro}$); 7.07 (m, 2H, H$_{aro}$); 4.43 (d, J=5.9 Hz, 2H, CH$_2$); 3.48 (s, 2H, CH$_2$); 2.68 (t, J=5.6 Hz, 2H, CH$_2$); 2.47 (t, J=5.5 Hz, 2H, CH$_2$); 2.21 (s, 3H, CH$_3$). $^{13}$C NMR (75 MHz, CDCl$_3$) δ: 172.7 (CO); 144.4 (C$_{aro}$); 137.5 (C$_{aro}$); 132.4 (C$_{aro}$); 129.0 (C$_{aro}$); 128.5 (C$_{aro}$); 128.1 (C$_{aro}$); 127.5 (C$_{aro}$); 118.8 (C$_{aro}$); 110.9 (C$_{aro}$); 62.2 (CH$_2$); 52.9 (CH$_2$); 42.5 (CH$_3$); 41.1 (CH$_2$); 32.6 (CH$_2$). LCMS m/z 308.0 [M+H]$^+$.

Example 36: Synthesis of N-(2,4-Dichlorobenzyl)-3-(benzylmethylamino)propanamide (compound 3.4d)

The compound 3.4d was synthesized according to the procedure E3 by using N-(4-chlorobenzyl)-3-chloropropanamide 2.3d (0.37 mmol, 100 mg) and N-benzylmethylamine (3.7 mmol, 483 µL). Purification by thick layer chromatography (DCM:MeOH(NH$_3$), 9.7:0.3 (v/v)). Yield: 80%. $^1$H NMR (300 MHz, CDCl$_3$), δ: 8.90 (br s, 1H, NH); 7.38 (d, J=1.9 Hz, 1H, H$_{aro}$); 7.28 (d, J=8.3 Hz, 1H, H$_{aro}$); 7.27-7.15 (m, 4H, H$_{aro}$); 7.10 (m, 2H, H$_{aro}$); 4.45 (d, J=5.8 Hz, 2H, CH$_2$); 3.50 (s, 2H, CH$_2$); 2.70 (t, J=6.1 Hz, 2H, CH$_2$); 2.45 (t, J=5.6 Hz, 2H, CH$_2$); 2.18 (s, 3H, CH$_3$). $^{13}$C NMR (75 MHz, CDCl$_3$) δ: 172.5 (CO); 137.5 (C$_{aro}$); 134.8 (C$_{aro}$); 134.3 (C$_{aro}$); 133.7 (C$_{aro}$); 131.1 (C$_{aro}$); 129.2 (C$_{aro}$); 129.0 (C$_{aro}$); 128.4 (C$_{aro}$); 127.5 (C$_{aro}$); 127.3 (C$_{aro}$); 62.2 (CH$_2$); 53.1 (CH$_2$); 41.0 (CH$_3$); 40.5 (CH$_2$); 32.6 (CH$_2$). LCMS m/z 350.97, 354.96, 352.93 [M+H]$^+$.

Example 37: Synthesis of N-(3-Chlorobenzyl)-3-(benzylmethylamino)propanamide (Compound 3.4e)

The compound 3.4e was synthesized according to the procedure E3 by using N-(4-chlorobenzyl)-3-chloropropanamide 2.3e (0.43 mmol, 100 mg) and N-benzylmethylamine (4.3 mmol, 555 µL). Purification by thick layer chromatography (DCM:MeOH(NH$_3$), 9.7:0.3 (v/v)). Yield: 68%. $^1$H NMR (300 MHz, CDCl$_3$), δ: 8.80 (br s, 1H, NH); 7.30-7.00 (m, 9H, H$_{aro}$); 4.40 (d, J=5.6 Hz, 2H, CH$_2$); 3.50 (s, 2H, CH$_2$); 2.70 (t, J=6.0 Hz, 2H, CH$_2$); 2.48 (t, J=5.6 Hz, 2H, CH$_2$); 2.20 (s, 3H, CH$_3$). $^{13}$C NMR (75 MHz, CDCl$_3$) δ: 172.5 (CO); 140.8 (C$_{aro}$); 137.5 (C$_{aro}$); 134.4 (C$_{aro}$); 129.9 (C$_{aro}$); 129.0 (C$_{aro}$); 128.5 (C$_{aro}$); 127.8 (C$_{aro}$); 127.5 (C$_{aro}$); 127.4 (C$_{aro}$); 125.9 (C$_{aro}$); 62.2 (CH$_2$); 53.1 (CH$_2$); 42.5 (CH$_3$); 40.1 (CH$_2$); 32.6 (CH$_2$). LCMS m/z 317.1, 319.1 [M+H]$^+$.

Compounds have been transformed into their hydrochloride salts by solubilizing in MeOH, treating with HCl 1M until pH=1 and then lyophilizing.

Biology Examples

1. Binding Assay to σ Receptors

The σ binding assays were performed according to Ganapathy et al. (Ganapathy, M. E.; Prasad, P. D.; Huang, W.; Seth, P.; Leibach, F. H.; Ganapathy, V. Molecular and ligand-binding characterization of the sigma-receptor in the Jurkat human T lymphocyte cell line. *J. Pharmacol. Exp. Ther.* 1999, 289, 251-260). The σ$_1$ binding assay was carried out by incubating Jurkat cell membranes (10-20 mg protein per tube) with [$^3$H](+)-pentazocine (15 nM) and a range of concentrations of tested compounds, at 37° C. for 2 hours, in 5 mM Tris/HCl buffer (pH=7.4). The σ$_2$ binding assay was performed by incubating Jurkat cell membranes (10-20 mg protein per tube) with [$^3$H]-DTG (25 nM) in presence of (+)-pentazocine (1 µM) to saturate σ$_1$ receptors, and a range of concentrations of tested compounds, at room temperature for 1 hour in 5 mM Tris/HCl buffer (pH=7.4). The final assay volume was 0.5 mL. Binding was terminated by rapid filtration through Wathman GF/B filters, which were then washed with 5×1 mL ice-cold NaCl solution and allowed to dry before bound radioactivity was measured using liquid scintillation counting. Nonspecific binding was determined, in both assays, under similar conditions, but in presence of 10 µM unlabeled haloperidol. Inhibition constants (K$_i$) were calculated from the IC$_{50}$ values according to the method of Cheng and Prusoff (Cheng, Y.; Prusoff, W. H. Relationship between the inhibition constant (K$_i$) and the concentration of inhibitor which causes 50 percent inhibition (IC$_{50}$) of an enzymatic reaction. *Biochem Pharmacol.* 1973, 22 (23), 3099-108):

$$K_i = \frac{IC_{50}}{1 + \frac{L}{K_d}}$$

Where IC$_{50}$=Inhibitory concentration at 50%
L=Concentration of radioligand
Kd=Affinity constant of radioligand The σ$_1$ binding assay was carried out with [$^3$H](+)-pentazocine (L=15 nM, K$_d$=16 nM) as radioligand and the σ$_2$ binding assay with [$^3$H]-DTG (L=25 nM, K$_d$=80.84 nM).

The results of the sigma-1 and sigma-2 binding assays (i.e. the mean K$_i$ values for 2 or 3 independent experiments with less than 10% deviation) are shown in Tables 2, 3 and 4 hereafter:

TABLE 2

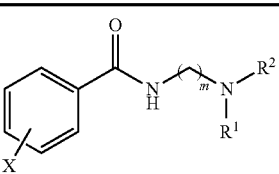

| Compound No.* | X | m | —NR$_1$R$_2$ | Sigma 1 K$_i$ (nM) | Sigma 2 K$_i$ (nM) | Ratio σ$_2$/σ$_1$ |
|---|---|---|---|---|---|---|
| 3.1.2 | 4-n-Pr | 3 | —N(CH$_3$)(CH$_2$Ph) | 3.7 | 160 | 43 |

TABLE 2-continued

Structure: benzamide with X substituent, -C(=O)-NH-(CH2)m-NR1R2

| Compound No.* | X | m | —NR₁R₂ | Sigma 1 $K_i$ (nM) | Sigma 2 $K_i$ (nM) | Ratio $\sigma_2/\sigma_1$ |
|---|---|---|---|---|---|---|
| 3.1.3 | 4-n-Bu | 3 | N-methyl-N-benzyl | 7.3 | 49 | 7 |
| 3.1.4 | 4-t-Bu | 3 | N-methyl-N-benzyl | 1.6 | nd | |
| 3.1.5 | 4-CF₃ | 3 | N-methyl-N-benzyl | 1.4 | 98 | 70 |
| 3.1.6 | 4-F | 3 | N-methyl-N-benzyl | 20 | 470 | 24 |
| 3.1.7 | 2-Cl | 3 | N-methyl-N-benzyl | 47 | >1200 | >26 |
| 3.1.8 | 3-Cl | 3 | N-methyl-N-benzyl | 10 | 340 | 34 |
| 3.1.9 | 4-Cl | 2 | N-methyl-N-benzyl | 3.6 | 850 | 236 |
| 3.1.10 | 4-Cl | 3 | N-methyl-N-benzyl | 3.2 | 190 | 60 |
| 3.1.11 | 4-Cl | 4 | N-methyl-N-benzyl | 1.7 | 20 | 12 |
| 3.1.12 | 4-Cl | 3 | N-methyl-N-phenethyl | 4.3 | 200 | 47 |
| 3.1.15 | 4-Cl | 3 | isoindolinyl | 19 | nd | |
| 3.1.20 | 2-Br | 3 | N-methyl-N-benzyl | 42 | >1200 | >29 |
| 3.1.21 | 3-Br | 3 | N-methyl-N-benzyl | 3.9 | 350 | 90 |
| 3.1.22 | 4-Br | 3 | N-methyl-N-benzyl | 2.1 | 160 | 76 |
| 3.1.23 | 2,3-Cl | 3 | N-methyl-N-benzyl | 10 | 310 | 31 |
| 3.1.24 | 2,4-Cl | 3 | N-methyl-N-benzyl | 1.3 | 310 | 238 |
| 3.1.25 | 3,4-Cl | 3 | N-methyl-N-benzyl | 1.1 | 59 | 54 |
| 3.1.26 | 3,5-Cl | 3 | N-methyl-N-benzyl | 23 | 48 | 2 |

TABLE 2-continued

| Compound No.* | X | m | —NR₁R₂ | Sigma 1 $K_i$ (nM) | Sigma 2 $K_i$ (nM) | Ratio $\sigma_2/\sigma_1$ |
|---|---|---|---|---|---|---|
| 3.1.27 | 2-F-4-Br | 3 | | 2.9 | Nd | |
| 3.1.28 | 3-OCH₃ | 3 | | 40 | >1200 | >30 |
| 3.1.29 | 4-OCH₃ | 3 | | 37 | >1000 | >27 |
| 3.1.30 | 3-N(CH₃)₂ | 3 | | 1.9 | | |
| 3.1.31 | 4-CN | 3 | | 24 | >1200 | >50 |
| 3.1.32 | 4-NO₂ | 3 | | 4.3 | 360 | 84 |
| 3.1.34 | 3,4-Cl | 2 | | 6.5 | 110 | 17 |
| 3.1.36 | 4-CN | 2 | | 1.2 | 170 | 142 |
| 3.1.37 | 4-NO₂ | 2 | | 3.6 | 1400 | 389 |

*: compounds are evaluated as their hydrochloride salts.

TABLE 3

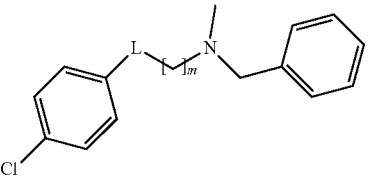

| Compound No.* | L | m | Sigma 1 $K_i$ (nM) | Sigma 2 $K_i$ (nM) | Ratio $\sigma_2/\sigma_1$ |
|---|---|---|---|---|---|
| 3.2a | SO₂NH | 3 | 5.8 | 200 | 35 |
| 3.3a | NHCO | 3 | 6.5 | 170 | 26 |
| 3.4a | CH₂NHCO | 2 | 1.7 | 410 | 241 |
| 3.5a | CH₂NH | 3 | 2.9 | nd | — |

*: compounds are evaluated as their hydrochloride salts.

TABLE 4

| Compound No.* | $(X)_n$ | Sigma 1 $K_i$ (nM) | Sigma 2 $K_i$ (nM) | Ratio $\sigma_2/\sigma_1$ |
|---|---|---|---|---|
| 3.4b | 4-NO₂ | 2.3 | 6500 | 2826 |
| 3.4c | 4-CN | 5.6 | 1800 | 321 |
| 3.4d | 2,4-Cl | 2.3 | 120 | 52 |
| 3.4e | 3-Cl | 0.63 | 200 | 317 |

*: compounds are evaluated as their hydrochloride salts.

The present study shows that the compounds of the invention have good sigma1 affinities and are selective over sigma 2. Especially compounds 3.1.9, 3.1.24, 3.4b and 3.5a have sigma 1 affinities in the nanomolecular range (1.3 to 3.6 nM) and excellent sigma 2/sigma 1 selectivities between 236 and 2826.

2. Agonist Activity of Sigma-1 Receptor Ligand 3.1.10 in the Dizocilpine-Induced Learning Deficits Test The activity of compound 3.1.10 was evaluated on the prevention of the dizocilpine-induced learning deficits measured using two behavioral tests. The present experiment tested if its anti-amnesic activity could be blocked by pre-treatment with the reference sigma-1 receptor antagonist NE-100.

2.1 Study Plan—Protocols and Materials
2.1.1. Experimental Design
Sixty (60) mice were used. Behavioral testing started one week after the arrival of the animals in the AMYLGEN animal facility.
5 treatment groups were designed and used as follows:

| Treatment group | n |
|---|---|
| 1. vehicle 1 + vehicle 2 | 12 |
| 2. dizocilpine + vehicle 2 | 12 |

| Treatment group | n |
|---|---|
| 3. dizocilpine (0.15 mg/kg i.p.) + Cpd. 3.1.10 (0.5 mg/kg) | 12 |
| 4. dizocilpine (0.15 mg/kg i.p.) + Cpd. 3.1.10 (0.5 mg/kg)+ | 12 |
| 5. dizocilpine (0.15 mg/kg i.p.) + NE-100 (3 mg/kg) | 12 |
| Total mice | 60 |

Vehicle 1 was physiological saline for dizocilpine, DMSO 2% in water for compound 3.1.10

Animals were used at day 1 in the Y-maze test and at days 2 and 3 in the passive avoidance test, with training at day 2 and retention at day 3.

Test compounds, compound 3.1.10 and/or NE-100 were administered 10 min before dizocilpine (at 0.15 mg/kg i.p.) or vehicle.

Dizocilpine or vehicle 1 was administered 20 min before the Y-maze test session on day 1.

Dizocilpine or vehicle 1 was administered 20 min before the passive avoidance training session on day 2. Drugs were not injected before the retention session on day 3.

The whole experiment program was performed in a single series experiment.

Treatments were randomized.

2.1.2. Animals

Male Swiss mice, 6 weeks old and weighing 30-35 g, from JANVIER (Saint Berthevin, France), were housed in groups with access to food and water ad libitum, except during experiments. They were kept in a temperature and humidity controlled animal facility on a 12 h/12 h light:dark cycle (lights on at 7:00 am). Behavioral experiments were carried out between 09:00 am and 05:00 pm, in a sound attenuated and air-regulated experimental room, to which mice were habituated at least 30 min. Mice were numbered by marking their tail using permanent markers ad sacrificed immediately after the passive avoidance retention session.

2.1.3. Test Compounds

Compound 3.1.10 of Example 10 above.

Dizocilpine ((+)-MK-801 maleate, CAS #77086-22-7, batch 9A/124751) was from Tocris Bioscience.

NE-100 hydrochloride (CAS #149409-57-4, batch 1B/124951) was from Tocris Bioscience.

All compounds were injected intraperitoneally (i.p.) in a volume of 100 µL per 20 g of body weight, corresponding to 5 mL/kg.

2.1.4. Randomization of the Treatments

Treatment received by animals tested in series were conterbalanced.

2.1.5. Mortality

No animal deceased following injection or during the behavioral testing.

2.2. Behavioral Analyses 2.2.1. Spontaneous Alternation Performances

Animals were tested for spontaneous alternation performance in the Y-maze, an index of spatial working memory. The Y-maze is made of grey polyvinylchloride. Each arm is 40 cm long, 13 cm high, 3 cm wide at the bottom, 10 cm wide at the top, and converging at an equal angle. Each mouse was placed at the end of one arm and allowed to move freely through the maze during an 8 min session. The series of arm entries, including possible returns into the same arm, were checked visually. An alternation was defined as entries into all three arms on consecutive occasions. The number of maximum alternations was therefore the total number of arm entries minus two and the percentage of alternation was calculated as: (actual alternations/maximum alternations)× 100. Parameters included the percentage of alternation (memory index) and total number of arm entries (exploration index).

Animals showing an extreme behavior (alternation <20% or >90% or number of arm entries<10) are usually discarded from the calculations. 2 animals were discarded accordingly.

2.2.2. Step-Through Passive Avoidance Test

The apparatus is a two-compartments (15×20×15 cm high) box with one illuminated with white polyvinylchloride walls and the other darkened with black polyvinylchloride walls and a grid floor. A guillotine door separates each compartment. A 60 W lamp positioned 40 cm above the apparatus lights up the white compartment during the experiment. Scrambled footshocks (0.3 mA for 3 s) could be delivered to the grid floor using a shock generator scrambler (Lafayette Instruments, Lafayette, USA). The guillotine door is initially closed during the training session. Each mouse was placed into the white compartment. After 5 s, the door was raised. When the mouse entered the dark compartment and placed all its paws on the grid floor, the door was closed and the footshock delivered for 3 s. The step-through latency (the latency spent to enter the dark compartment) and the number of vocalizations was recorded. The retention test was carried out after 24 h. Each mouse was placed again into the white compartment. After 5 s, the door was opened. The step-through latency was recorded up to 300 s. When the mouse entered the dark compartment or 300 s has elapsed (they were therefore manually placed in it), the escape latency (latency to exit from the dark compartment) was recorded up to 300 s.

2.2.3. Statistical Analyses

All values, except passive avoidance latencies, were expressed as mean±S.E.M. Statistical analyses were performed using two-way ANOVA (F value), with genotype and peptide treatment as independent factors, followed by a Dunn's post-hoc multiple comparison test.

Passive avoidance latencies do not follow a Gaussian distribution, since upper cut-off times are set. They were therefore analyzed using a Kruskal-Wallis non-parametric ANOVA (H value), followed by a Dunn's multiple comparison test.

$p<0.05$ was considered as statistically significant.

2.3. Results

The results of the spontaneous alternation and passive avoidance assays are represented in FIGS. 1a and 1b.

Compound 3.1.10 significantly attenuated the dizocilpine-induced learning deficits, at 0.5 mg/kg in the Y-maze test and in the passive avoidance test. The beneficial effect of compound 3.1.10 in the two tests was prevented by treatment with the sigma-1 antagonist NE-100 at 3 mg/kg, devoid of effect by itself.

These results thus demonstrate the sigma-1 receptor effect of compound 3.1.10.

3. In Vivo Assay to Assess Activity of Compound 3.1.10 in Rodent MS Model

Experimental autoimmune encephalomyelitis (EAE) is an unequivocal animal model of multiple sclerosis (MS), a demyelitating disabling disease of the central nervous system characterized by the inappropriate effect of reactive T and B cells.

Materials and Methods

Animals.

SJL/J mice were purchased from Janvier (Le Genest-St-Isle, France) and bred under conventional barrier protection at the Pasteur Institute (Lille, France). All experiment protocols and procedures were in compliance with the European Communities Council Directives of 24 Nov. 1986 (86/609/EEC) and were approved by the local ethical committee (CEEA 102009R). Efforts were made to minimize the number of animals used and their suffering. Animals that reached severe hind limb paresis (clinical grade 3) were isolated, and hydration and food access were facilitated.

EAE Induction and Treatment.

The method of EAE induction was similar to previously published methods (Lee-Chang et al., Immunol Lett. 2011 Mar. 30; 135(1-2):108-17). Randomized 9-week-old female SJL/J mice were inoculated subcutaneously (s.c.) in the neck with an emulsion containing 100 μg of myelin proteolipid protein $(PLP)_{139-151}$ peptide and an equal volume of Freund's complete adjuvant (FCA) containing 4 mg/ml of heat-inactivated *Mycobacterium tuberculosis* H37RA (Difco Laboratories, Detroit, Mich., USA) on day 0. Additionally, mice received 0.3 μg of *Bordetella pertussis* toxin (BPT) (Sigma-Aldrich, Saint Louis, Mich., USA) intraperitoneally (i.p.) on days 0 and 3. Sham animals only received saline injection. SJL/J mice that only received FCA and BPT were also included in the experiments.

Compound 3.1.10 was dissolved in physiological saline. Control animals received one administration of saline solution (vehicle).

For validation of the σ1 action, pretreatment BD1047 (N'-[2-(3,4-dichlorophenyl)ethyl]-N,N,N'-trimethylethane-1,2-diamine; Costa B. R., Radesca L., Di Paolo L., Bowen W. D. J. Med. Chem. 1992, 35, 38-47) or saline, i.p.) was administered 20 min prior to receiving compound 3.1.10 (i.p.). Injections were performed on the onset of EAE (i.e. grade=2) and continued for the following 14 days. The clinical course was followed for 35 days. Three different groups, EAE-vehicle, EAE-compound 3.1.10 (1 mg/kg), and EAE-DB1047 (10 mg/kg) compound 3.1.10 (1 mg/kg) were used per experiment with 7 animals per treatment group.

For preventive treatment, single compound 3.1.10 i.p. injection was performed on day 0 (D0). Three different groups, EAE-vehicle, EAE-compound 3.1.10 (0.5 mg/kg), and EAE-compound 3.1.10 (1 mg/kg), were used per experiment with 13-15 animals per treatment group.

For curative treatment, p.o. administrations were performed on the onset of EAE (i.e. grade=2) and treatment was continued for the following 14 days. The clinical course was followed for 70 days. Three different groups, EAE-vehicle, EAE-compound 3.1.10 (0.5 mg/kg), and EAE-compound 3.1.10 (1 mg/kg), were used per experiment with 7 animals per treatment group.

Mice showed no apparent toxic side effects of any treatment protocols.

Clinical Evaluation.

Body weight and clinical signs of EAE were monitored daily. The severity of clinical symptoms was scored based on a standard neurological scoring system for EAE, as follows: grade 0, no disease; grade 1, moderate tail hypotonia and/or slight clumsy gait; grade 2, tail atony and/or clumsy gait; grade 3, severe hind limb paresis; grade 4, paraplegia; grade 5, tetraplegia. Scoring was performed in a blind fashion.

Serum Anti-PLP Enzyme-Linked Immunosorbent Assay (ELISA).

Mice were deeply anesthetized with an i.p. injection of pentobarbital. Serum samples were prepared from peripheral blood obtained by cardiac puncture immediately before perfusion. Active immunizations were verified by measuring anti-$PLP_{139-151}$ IgG antibody (Ab), as previously described (El Behi et al., (2007), J Neuroimmunol 182:80-8).

Results

The validation of σ1 action assay confirms that compounds of the invention are active via the σ1 receptor. The results are represented in FIG. 2.

The assay using compound 3.1.10 in preventive treatment demonstrates that compounds of the invention are useful in delaying the onset of EAE in mice. The results are represented in FIG. 3.

The assay using compound 3.1.10 in curative treatment demonstrates that compounds of the invention are useful in alleviating the symptoms of EAE in mice. The results are represented in FIG. 4.

EAE being an unequivocal animal model of multiple sclerosis (MS), a demyelitating disabling disease of the central nervous system characterized by the inappropriate effect of reactive T and B cells, the above results show the usefulness of the compounds of the invention, especially of compound 3.1.10, in the treatment and prevention of multiple sclerosis (MS) in particular and σ1 receptor related diseases in general.

While embodiments of the invention have been illustrated and described, it is not intended that these embodiments illustrate and describe all possible forms of the invention. Rather, the words used in the specification are words of description rather than limitation ant it is understood that various changes may be made without departing from the spirit and scope of the invention.

The invention claimed is:

1. A compound of Formula I:

(I)

or a pharmaceutically acceptable salt or solvate thereof, wherein $X^1$ and $X^5$ are independently selected from the group consisting of hydrogen, halogen, C1-C4-alkyl, C1-C4-haloalkyl, cyano, nitro, di(C1-C4-alkyl)amino, —NHCOOR', and —COOR', wherein R' is methyl, ethyl, n-propyl, n-butyl, iso-propyl, iso-butyl or tert-butyl;

$X^2$, $X^3$, $X^4$ are independently selected from the group consisting of hydrogen, chloro, C1-C4-alkyl, C1-C4-haloalkyl, C1-C4-alkoxy, cyano, nitro, di(C1-C4-alkyl) amino, —NHCOOR', and —COOR', wherein R' is methyl, ethyl, n-propyl, n-butyl, iso-propyl, iso-butyl or tert-butyl; with the proviso that at least one of $X^1$, $X^2$, $X^3$, $X^4$, $X^5$ is not hydrogen and that at least one of $X^2$, $X^3$, $X^4$ is not C1-C4-alkoxy;

L is —NHC(O) or —NHSO$_2$;

n is 1;

m is 2, 3, 4 or 5;

$R^1$ is alkyl, and $R^2$ is 5- or 6-membered arylalkyl, 5- or 6-membered cycloalkylalkyl, wherein the cyclic moiety of said arylalkyl or cycloalkylalkyl is optionally substituted by one or more fluoro; or R¹ and R² together with the nitrogen atom to which they are attached, form a isoindolinyl group optionally substituted by one or more substituents independently selected from C1-C2 alkyl and halogen.

2. The compound according to claim 1 or a pharmaceutically acceptable salt or solvate thereof, wherein n is 1 and L is —NHC(O)—.

3. The compound according to claim 1, or a pharmaceutically acceptable salt or solvate thereof, wherein R¹ is methyl.

4. The compound according to claim 1, or a pharmaceutically acceptable salt or solvate thereof, wherein R² is 5- or 6-membered aryl-C1-C2-alkyl.

5. The compound according to claim 1, or a pharmaceutically acceptable salt or solvate thereof, wherein m is 2, 3 or 4.

6. The compound according to claim 1, having Formula III

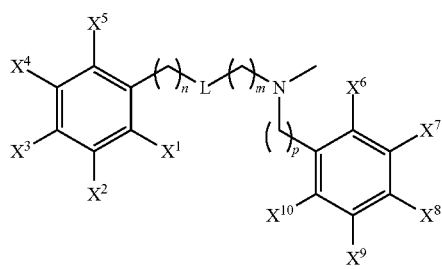

or a pharmaceutically acceptable salt or solvate thereof, wherein
$X^1$, $X^2$, $X^3$, $X^4$, $X^5$, L, n and m are as defined in claim 1;
p is 1 or 2;
$X^6$, $X^7$, $X^8$, $X^9$, $X^{10}$ are independently selected from H and fluoro.

7. The compound according to claim 1, having Formula V

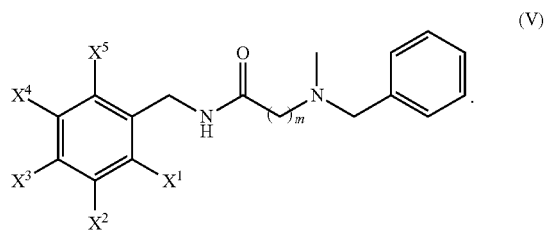

8. The compound according to claim 1 selected from the group consisting of:
N-[3-(benzylmethylamino)propyl]-4-chlorobenzensulfonamide,
4-(benzylmethylamino)-N-(4-chlorophenyl)butanamide,
N-(4-chlorobenzyl)-3-(benzylmethylamino)propanamide,
N-(4-nitrobenzyl)-3-(benzylmethylamino)propanamide,
N-(4-cyanobenzyl)-3-(benzylmethylamino)propanamide,
N-(2,4-dichlorobenzyl)-3-(benzylmethylamino)propanamide, and
N-(3-chlorobenzyl)-3-(benzylmethylamino)propanamide.

9. A pharmaceutical composition comprising an effective amount of compound according to claim 1.

* * * * *